US006558951B1

(12) United States Patent
Tomai et al.

(10) Patent No.: US 6,558,951 B1
(45) Date of Patent: May 6, 2003

(54) MATURATION OF DENDRITIC CELLS WITH IMMUNE RESPONSE MODIFYING COMPOUNDS

(75) Inventors: Mark A. Tomai, Oakdale, MN (US); John P. Vasilakos, Woodbury, MN (US); Cory L. Ahonen, Hanover, NH (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/248,439

(22) Filed: Feb. 11, 1999

(51) Int. Cl.$^7$ .............................. C12N 5/00; C12N 5/02

(52) U.S. Cl. ................. 435/377; 435/375; 435/384; 435/325; 514/291; 546/82

(58) Field of Search ................. 435/375, 377, 435/384, 325; 514/291; 546/82

(56) References Cited

U.S. PATENT DOCUMENTS 5,851,756 A    12/1998  Steinman et al.

FOREIGN PATENT DOCUMENTS

| WO | 93/20847 | 10/1993 |
|---|---|---|
| WO | 98/23728 | 6/1998 |

OTHER PUBLICATIONS

Gibson, SJ et al. J. Interfero and Cytokine Res. 15(6):537–545, Jun. 1995.*
Zitvogel 1 et al.: "IL–12–Engineered Dendritic Cells Serve as Effective Tumor Vaccine Adjuvants in Vivo*" Annals of The New York Academy of Sciences, New York, NY US, vol. 795, 1996, pp. 284–293, XP–000867039.
Ahonen, et al, "Dendritic Cell Maturation and Subsequent enhanced T–cell Stimulation Induced with the Novel Synthetic Immune Response Modifier R–848", Cellular Immunology, vol. 197, No. 1, Oct. 10, 1999, p. 62–72.
Tohoku, J., "Maturation of Dendritic Cells Induced by Cytokines and Haptent", Exp. Med., pp 159–172, Tohoku University Medical Press (1988).
Jonuleit, Helmut; Knop, Jurgen; Enk, Alexander H., "Cytokines and Their Effects on Maturaiton, Differentiation and Migration of Dendritic Cells", Arch Dermatol Res, pp 1–8, Springer–Verlag (1996).
Jonuleit, et al, "Pro–inflammatory Cytokines and Prostaglandins Induce Maturation of Potent Immunostimulatory Dendritic Cells Under Fetal Calf Serum–free Conditions", Eur. J. Immunol, pp 3135–3142, Wiley–VCH Verlag GmbH, D–69451 Weinheim, (1997).
Romani, et al, "Generation of Mature Dendritic Cells from Human Blood an Improved Method with Special Regard to Clinical Applicability", Journal of Immunological Methods, vol. 196, pp 137–151, Elsevier Science B.V., (1996).
Luft, et al, "Type I IFNs Enhance the Terminal Differntiation of Dendritic Cells", Journal of Immunology, pp 1947–1953, The American Assiciation of Immunologists, (1998).
Bender, et al, "Improved Methods for the Generation of Dendritic Cells from Nonproliferating progenitors in Human Blood", Journal of Immunological Methods, pp 121–135, Elsevier Science B.V., (1996).
Cella, et al, "Origin, maturation and Antigen Presenting Function of Dendritic Cells", Current Opinion in Immunology, vol. 9, pp 10–16, Current Biology Ltd, (1997).
Grabbe S, et al, "Tumor Antigen Presentation by Murine Epidermal Cells". J Immunol 146:3656–3661. No. 10, (May 15, 1991).
Flamand V, et al, "Murine Dendritic Cells Pulsed in Vitro with Tumor Antigen Induced Tumor Resistance in Vivo", Eur J Immunol, 24: 605–610. (1995).
Steinman RM. 1991. "The Dendritic Cell System and its Role in Immunogenicity". Ann Rev Immunol, 1:143–.
Romani N, et al, "Proliferating Dendritic Cell Progenitors in Human Blood". J Exp Med, 180: 83–93, (Jul. 1994).
Inaba K, et al, "Generation of Large Numbers of Dendritic Cells from Mouse Bone Marrow Cultures Supplemented with Granulocyte/macrophage Colony–stimulating Factor". J Exp Med, 176: 1693–1702. (Dec. 1992).
Lanier LL, et al D80 (B7) and CD86 (B70) Provide Costi Signals for T Cell Proliferation, Cytokine Production, and Generation of CTL J Immunol, 15 105. (1995).
Bhardwaj N, et al, "IL–12 in Conjuction with Dendritic Cells Enhances Antiviral CD8+CTL Responses", J Clin Invest, 98: 715–722. (Aug. 1996).
Tuting T, et al, "Autologous Human Monocyte–derived Dendritic Cells Genetically Modified to Express Melanoma Antigens Elicit Primary Cytotoxic T Cell Responses in Vitro: Enhancement by Cotransfection of Genes Encoding the Th1–biasing Cytokines IL–12 and IFN–α", J Immunol, 160: 1139–1147. (1998).
Slade HB, Owens ML, Tomai MA, Miller RL. 1998. "Imiquimod 5% Cream (Aldara™)", Exp Opin Invest Drugs, 7: 437–449.
Tomai MA, et al, "Imiquimod: In Vivo and In Vitro Characteristics and Toxicology", Cutaneous infection and therapy. New York, Marcel Dekker, Inc. pp 405–415, (1997).
Tomai, M.A., Immunomodulating and Antiviral Activities of the Imidazoquinoline S–28463. Antiviral Res, 28: 253, (1995).

* cited by examiner

Primary Examiner—Patrick J. Nolan
Assistant Examiner—Gerald R. Ewoldt
(74) Attorney, Agent, or Firm—Christopher D. Gram; MarySusan Howard; Ted K. Ringsred

(57) ABSTRACT

A method of inducing the maturation of dendritic cells by stimulating immature dendritic cells with an imidazoquinoline type immune response modifying compound. Dendritic cells that have been matured in this manner display increased antigen presenting ability and may be used as immunotherapeutic agents.

10 Claims, 9 Drawing Sheets

US 6,558,951 B1

MATURATION OF DENDRITIC CELLS WITH IMMUNE RESPONSE MODIFYING COMPOUNDS

FIELD OF THE INVENTION

The invention relates to the use of synthetic immune response modifiers to induce the maturation of dendritic cells in vitro. The invention additionally relates to methods of maturing dendritic cells, to methods of enhancing the antigen presenting ability of dendritic cells, and of enhancing T-cell stimulation using synthetic immune response modifiers. The invention further relates to cellular adjuvants prepared with the dendritic cells that have been matured according to the method of the invention.

BACKGROUND OF THE INVENTION

Dendritic cells are known to play an important role in the immune system, both for their potent antigen presenting ability and their ability to initiate T-cell mediated immune responses. Indeed, dendritic cells ("DC") activate T-cells more efficiently than any other known antigen presenting cell, and may be required for the initial activation of naïve T-cells in vitro and in vivo. These cells are generally present in the body at locations that are routinely exposed to foreign antigens, such as the skin, lung, gut, blood, and lymphoid tissues. In general, DC are broadly classified as immature or mature. Immature DC endocytose and process antigen efficiently, but express low levels of costimulatory molecules. In contrast, mature DC display increased levels of costimulatory molecules CD40, CD80 and CD86, as well as HLA-DR. In addition, mature DC express CD83 and secrete increased amounts of various cytokines and chemokines that aid T-cell activation.

In addition to naive T-cell activation, DC can influence the balance of the Th1/Th2 immune response. Several reports have indicated that DC preferentially activate Th1 responses, with the major determining factor being IL-12 secretion from the activated DC. Macatonia et al., *J. Immunol.* 154:5071 (1995). Hilkens et al., *Blood* 90:1920 (1997). Other reports have shown that DC can induce the generation of either Th1 or Th2 clones. Roth, et al., *Scand. J. Immunol.* 43:646 (1996). The evidence indicates that multiple factors influence the ability of DC to initiate a Th1 or Th2 response, including the DC to T-cell ratio, the DC tissue of origin, the amount of antigen used to prime the DC, the expression of costimulatory molecules and the antigen injection route.

The pivotal role played by DC in antigen presentation and T-cell activation has resulted in considerable interest in the use of DC in immunotherapy. This is particularly evident in the areas of vaccinology and cancer immunotherapy. Although much effort has been devoted to the development of successful vaccines using recombinant DNA, successful clinical use of DNA vaccines has not been achieved. Recent evidence indicates that effective immunization with DNA vaccines requires recombinant protein expression from DC. Further, enhanced immunity in animal models has been achieved utilizing DNA vaccines that encode for cytokines or that contain CpG oligonucleotide sequences that upregulate DC maturation. Recently, autologous DC obtained from cancer patients have been used for cancer immunotherapy. See, e.g., WO98/23728. Accordingly, efficient ex vivo methods for generating DC are prerequisite for successful immunotherapy.

In general, the process of ex vivo DC generation consists of obtaining DC precursor cells and then differentiating the cells in vitro into DC before introduction back into the patient. However, the DC must be terminally differentiated, or they will de-differentiate into monocytes/macrophages and lose much of their immunopotentiating ability. Ex vivo DC maturation has been successfully accomplished with monocyte conditioned medium; recombinant cytokines such as TNF-$\alpha$, IL-1 and IL-6; bacterial products such as LPS, bacterial DNA and cross-linking CD40; and transfection with genes that encode cytokines or costimulatory molecules. While these methods are capable of producing mature DC, there are disadvantages to using recombinant molecules and cellular supernatants for maturing DC. These include inconsistent quality and yield from lot to lot of these reagents and the introduction of exogenous proteins into patients, which may be toxic or result in autoimmunity. Such reagents can also be expensive to produce, making the cost of immunotherapy prohibitively expensive. There is a need for a method of maturing DC in vitro that is reliable and efficient, without the drawbacks of the currently known methods.

SUMMARY OF THE INVENTION

We have found that certain immune response modifier (IRM) compounds can induce the maturation of DC in vitro. These compounds are small molecules that can be readily produced at a consistent, high level of purity and potency. By using these compounds one can efficiently and consistently mature DC, which can then be used as immunotherapeutic agents. The IRM compounds useful in the method of the invention are generally of the imidazoquinoline type; that is, they have a structure that contains the imidazoquinoline ring system or a similar ring system, such as imidazopyridine or imidazonaphthyridine.

Accordingly, the invention provides a method of in vitro maturation of dendritic cells comprising treating said dendritic cells with an imidazoquinoline type immune response modifying compound, as well as a population of dendritic cells produced by this method.

The invention further provides a method of enhancing the antigen presenting ability of dendritic cells comprising treating said dendritic cells with an imidazoquinoline type immune response modifying compound.

In addition, the invention provides a method of preparing a cellular adjuvant for the treatment of a disease comprising the steps of maturing dendritic cells in vitro by treating the dendritic cells with an imidazoquinoline type immune response modifying compound and exposing the mature dendritic cells to an antigen associated with said disease.

DETAILED DESCRIPTION OF THE INVENTION

The IRM Compounds

Figure 1A:
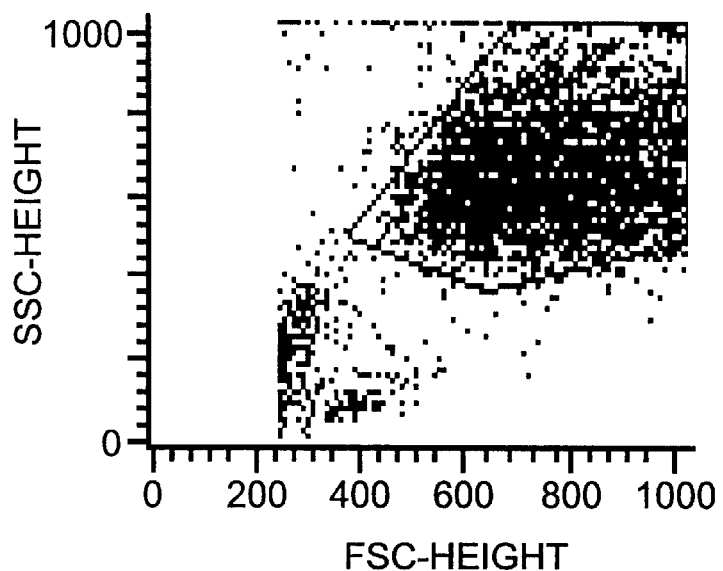
FIG. 1 is a graphical depiction of the ability of the IRM compound 4-amino-2-ethoxymethyl-$\alpha,\alpha$-dimethyl-1H-imidazo[4,5-c]quinolin-1-ethanol (R-848) to enhance cell surface expression of CD83 and CD86.

Compounds useful in the methods of the invention include imidazoquinoline type IRM compounds. In general, the term "imidazoquinoline type IRM compounds" refers to compounds containing an imidazoquinoline ring system or a similar ring system that have the ability to modify the immune response. Preferred imidazoquinoline type IRM compounds contain one or more of the following ring systems: imidazoquinoline; imidazopyridine; 6,7 fused cycloalkylimidazopyridine; 1,2-bridged imidazoquinoline; imidazonaphthyridine; and imidazotetrahydronaphthyridine. Particularly preferred IRM compounds contain an imidazoquinoline-4-amine ring system. Compounds useful in the methods of the invention will also typically have the ability to induce production of one or more of the cytokines TNF-α, IL-1, IL-6 and IL-12 when administered to a host or applied in vitro to dendritic cells or monocyte/macrophages.

Immune response modifier compounds useful in the method of the invention include compounds defined by Formulas I–IX(b) below. Preferred 1H-imidazo [4,5-c] quinolin-4-amines are defined by Formulas I–V:

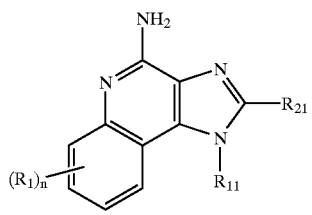

I wherein $R_{11}$ is selected from the group consisting of alkyl of one to ten carbon atoms, hydroxyalkyl of one to six carbon atoms, acyloxyalkyl wherein the acyloxy moiety is alkanoyloxy of two to four carbon atoms or benzoyloxy, and the alkyl moiety contains one to six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that if said benzene ring is substituted by two of said moieties, then said moieties together contain no more than six carbon atoms;

$R_{21}$ is selected from the group consisting of hydrogen, alkyl of one to eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that when the benzene ring is substituted by two of said moieties, then the moieties together contain no more than six carbon atoms; and each $R_1$ is independently selected from the group consisting of alkoxy of one to four carbon atoms, halogen, and alkyl of one to four carbon atoms, and n is an integer from 0 to 2, with the proviso that if n is 2, then said $R_1$ groups together contain no more than six carbon atoms;

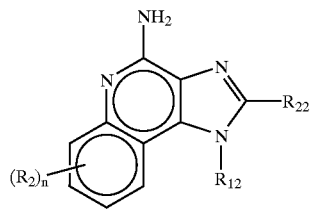

II wherein $R_{12}$ is selected from the group consisting of straight chain or branched chain alkenyl containing two to ten carbon atoms and substituted straight chain or branched chain alkenyl containing two to ten carbon atoms, wherein the substituent is selected from the group consisting of straight chain or branched chain alkyl containing one to four carbon atoms and cycloalkyl containing three to six carbon atoms; and cycloalkyl containing three to six carbon atoms substituted by straight chain or branched chain alkyl containing one to four carbon atoms; and $R_{22}$ is selected from the group consisting of hydrogen, straight chain or branched chain alkyl containing one to eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to four carbon atoms, straight chain or branched chain alkoxy containing one to four carbon atoms, and halogen, with the proviso that when the benzene ring is substituted by two such moieties, then the moieties together contain no more than six carbon atoms; and each $R_2$ is independently selected from the group consisting of straight chain or branched chain alkoxy containing one to four carbon atoms, halogen, and straight chain or branched chain alkyl containing one to four carbon atoms, and n is an integer from zero to 2, with the proviso that if n is 2, then said $R_2$ groups together contain no more than six carbon atoms;

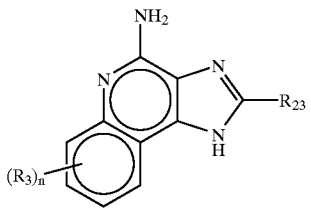

III wherein $R_{23}$ is selected from the group consisting of hydrogen, straight chain or branched chain alkyl of one to eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl of one to four carbon atoms, straight chain or branched chain alkoxy of one to four carbon atoms, and halogen, with the proviso that when the benzene ring is substituted by two such moieties, then the moieties together contain no more than six carbon atoms; and each $R_3$ is independently selected from the group consisting of straight chain or branched chain alkoxy of one to four carbon atoms, halogen, and straight chain or branched chain alkyl of one to four carbon atoms, and n is an integer from zero to 2, with the proviso that if n is 2, then said $R_3$ groups together contain no more than six carbon atoms;

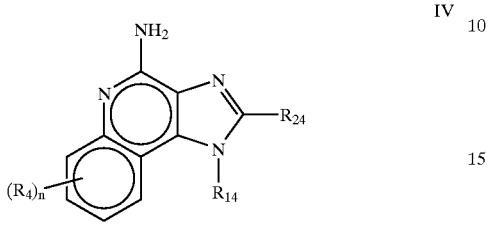

IV wherein $R_{14}$ is —$CHR_xR_y$ wherein $R_y$ is hydrogen or a carbon-carbon bond, with the proviso that when $R_y$ is hydrogen $R_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to four carbon atoms;

$R_{24}$ is selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen; and R4 is selected from the group consisting of hydrogen, straight chain or branched chain alkoxy containing one to four carbon atoms, halogen, and straight chain or branched chain alkyl containing one to four carbon atoms, and n is an integer from 0 to 2, with the proviso that if n is 2 then said $R_4$ groups together contain no more than six carbon atoms;

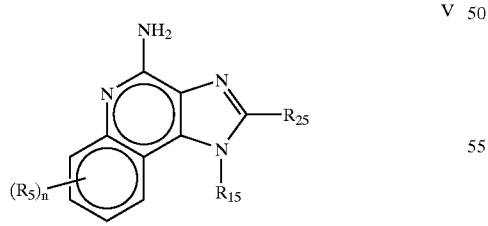

V wherein $R_{15}$ is selected from the group consisting of: hydrogen; straight chain or branched chain alkyl containing one to ten carbon atoms and substituted straight chain or branched chain alkyl containing one to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; straight chain or branched chain alkenyl containing two to ten carbon atoms and substituted straight chain or branched chain alkenyl containing two to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

$R_{25}$ is

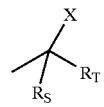

wherein $R_S$ and $R_T$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen;

X is selected from the group consisting of alkoxy containing one to four carbon atoms, alkoxyalkyl wherein the alkoxy moiety contains one to four carbon atoms and the alkyl moiety contains one to four carbon atoms, hydroxyalkyl of one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, alkylthio of one to four carbon atoms; and $R_5$ is selected from the group consisting of hydrogen, straight chain or branched chain alkoxy containing one to four carbon atoms, halogen, and straight chain or branched chain alkyl containing one to four carbon atoms, and n is an integer from 0 to 2, with the proviso that if n is 2, then said $R_5$ groups together contain no more than six carbon atoms.

Preferred 6,7 fused cycloalkylimidaiopyridine-4-amine IRM compounds are defined by Formula VI below:

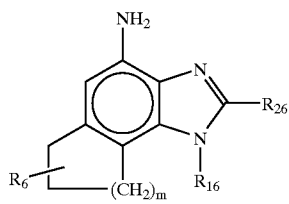

VI wherein m is 1, 2, or 3;

$R_{16}$ is selected from the group consisting of hydrogen; cycloalkyl of three, four, or five carbon atoms; straight chain or branched chain alkyl containing one to ten carbon atoms and substituted straight chain or branched chain alkyl containing one to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; fluoro- or chloroalkyl containing from one to ten carbon atoms and one or more fluorine or chlorine atoms; straight chain or branched chain alkenyl containing two to ten carbon atoms and substituted straight chain or branched chain alkenyl containing two to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

and —$CHR_xR_y$ wherein $R_y$ is hydrogen or a carbon-carbon bond, with the proviso that when $R_y$ is hydrogen $R_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to four carbon atoms, $R_{26}$ is selected from the group consisting of hydrogen, straight chain or branched chain alkyl containing one to eight carbon atoms, straight chain or branched chain hydroxyalkyl containing one to six carbon atoms, morpholinoalkyl wherein the alkyl moiety contains 1 to 4 carbon atoms, benzyl, (phenyl)ethyl and phenyl, the benzyl, (phenyl)ethyl or phenyl substituent being optionally substituted on the benzene ring by a moiety selected from the group consisting of methyl, methoxy, and halogen; and —$C(R_S)(R_T)(X)$ wherein $R_S$ and $R_T$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen;

X is selected from the group consisting of alkoxy containing one to four carbon atoms, alkoxyalkyl wherein the alkoxy moiety contains one to four carbon atoms and the alkyl moiety contains one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, alkylthio of one to four carbon atoms, halogen, hydroxy, morpholino, and morpholinoalkyl wherein the alkyl moiety contains one to four carbon atoms, and $R_6$ is selected from the group consisting of hydrogen, fluoro, chloro, straight chain or branched chain alkyl containing one to four carbon atoms, and straight chain or branched chain fluoro- or chloroalkyl containing one to four carbon atoms and at least one fluorine or chlorine atom.

Preferred imidazopyridine-4-amine IRM compounds are defined by Formula VII below:

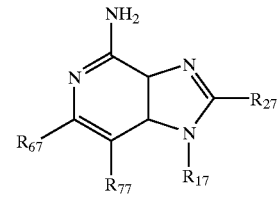

VII wherein $R_{17}$ is selected from the group consisting of hydrogen; —$CH_2R_W$ wherein $R_W$ is selected from the group consisting of straight chain, branched chain, or cyclic alkyl containing one to ten carbon atoms, straight chain or branched chain alkenyl containing two to ten carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, and phenylethyl; and —$CH=CR_ZR_Z$ wherein each $R_Z$ is independently straight chain, branched chain, or cyclic alkyl of one to six carbon atoms;

$R_{27}$ is selected from the group consisting of hydrogen, straight chain or branched chain alkyl containing one to eight carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, benzyl, (phenyl)ethyl and phenyl, the benzyl, (phenyl)ethyl or phenyl substituent being optionally substituted on the benzene ring by a moiety selected from the group consisting of methyl, methoxy, and halogen; and morpholinoalkyl wherein the alkyl moiety contains one to four carbon atoms; and $R_{67}$ and $R_{77}$ are independently selected from the group consisting of hydrogen and alkyl of one to five carbon atoms, with the proviso that $R_{67}$ and $R_{77}$ taken together contain no more than six carbon atoms, and with the further proviso that when $R_{77}$ is hydrogen then $R_{67}$ is other than hydrogen and $R_{27}$ is other than hydrogen or morpholinoalkyl, and with the further proviso that when $R_{67}$ is hydrogen then $R_{77}$ and $R_{27}$ are other than hydrogen.

Preferred 1,2-bridged imidazoquinoline-4-amine IRM compounds are defined by Formula VIII below:

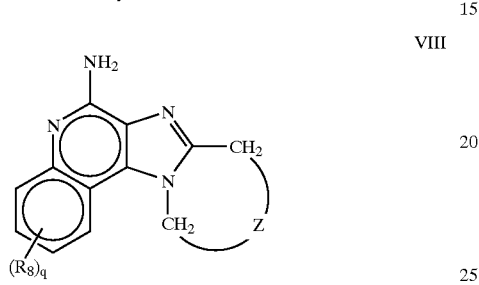

VIII wherein

Z is selected from the group consisting of:
—$(CH_2)_p$— wherein p is 1 to 4;
—$(CH_2)_a$—$C(R_DR_E)(CH_2)_b$—, wherein a and b are integers and a+b is 0 to 3, $R_D$ is hydrogen or alkyl of one to four carbon atoms, and $R_E$ is selected from the group consisting of alkyl of one to four carbon atoms, hydroxy, —$OR_F$ wherein $R_F$ is alkyl of one to four carbon atoms, and —$NR_GR'_G$ wherein $R_G$ and $R'_G$ are independently hydrogen or alkyl of one to four carbon atoms; and
—$(CH_2)_a$—$(Y)$—$(CH_2)_b$— wherein a and b are integers and a+b is 0 to 3, and Y is O, S, or —$NR_J$— wherein $R_J$ is hydrogen or alkyl of one to four carbon atoms;

and wherein q is 0 or 1 and $R_8$ is selected from the group consisting of alkyl of one to four carbon atoms, alkoxy of one to four carbon atoms, and halogen.

Preferred imidazonaphthyridine-4-amine and imidazotetrahydronaphthyridine-4-amine IRM compounds are defined by Formulas IX(a) and IX(b) below:

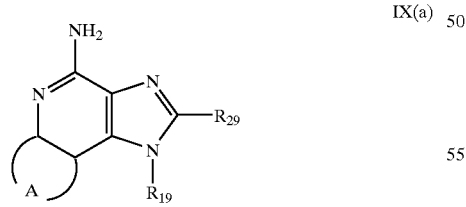

IX(a)

wherein

A is =N—CR=CR—CR=; =CR—N=CR—CR=; =CR—CR=N—CR=; or =CR—CR=CR—N=;

$R_{19}$ is selected from the group consisting of:
-hydrogen;
—$C_{1-20}$ alkyl or $C_{2-20}$ alkenyl that is unsubstituted or substituted by one or more substituents selected from the group consisting of:

-aryl;
-heteroaryl;
-heterocyclyl;
—O—$C_{1-20}$ alkyl,
—O—$(C_{1-20}$ alkyl$)_{0-1}$-aryl;
—O—$(C_{1-20}$ alkyl$)_{0-1}$-heteroaryl;
—O—$(C_{1-20}$ alkyl$)_{0-1}$-heterocyclyl;
—$C_{1-20}$ alkoxycarbonyl;
—$S(O)_{0-2}$—$C_{1-20}$ alkyl;
—$S(O)_{0-2}$—$(C_{1-20}$ alkyl$)_{0-1}$-aryl;
—$S(O)_{0-2}$—$(C_{1-20}$ alkyl$)_{0-1}$-heteroaryl;
—$S(O)_{0-2}$—$(C_{1-20}$ alkyl$)_{0-1}$-heterocyclyl;
—$N(R_{39})_2$;
—$N_3$;
oxo;
-halogen;
—$NO_2$;
—OH; and
—SH; and
—$C_{1-20}$ alkyl—$NR_{39}$—Q—X—$R_{49}$ or —$C_{2-20}$ alkenyl—$NR_{39}$—Q—X—$R_{49}$ wherein Q is —CO— or —$SO_2$—; X is a bond, —O— or —$NR_{39}$— and $R_{49}$ is aryl; heteroaryl; heterocyclyl; or —$C_{1-20}$ alkyl or $C_{2-20}$ alkenyl that is unsubstituted or substituted by one or more substituents selected from the group consisting of:
-aryl;
-heteroaryl;
-heterocyclyl;
—O—$C_{1-20}$ alkyl,
—O—$(C_{1-20}$ alkyl$)_{0-1}$-aryl;
—O—$(C_{1-20}$ alkyl$)_{0-1}$-heteroaryl;
—O—$(C_{1-20}$ alkyl$)_{0-1}$-heterocyclyl;
—$C_{1-20}$ alkoxycarbonyl;
—$S(O)_{0-2}$—$C_{1-20}$ alkyl;
—$S(O)_{0-2}$—$(C_{1-20}$ alkyl$)_{0-1}$-aryl;
—$S(O)_{0-2}$—$(C_{1-20}$ alkyl$)_{0-1}$-heteroaryl;
—$S(O)_{0-2}$—$(C_{1-20}$ alkyl$)_{0-1}$-heterocyclyl;
—$N(R_{39})_2$;
—$NR_{39}$—CO—O—$C_{1-20}$ alkyl;
—$N_3$;
oxo;
-halogen;
—$NO_2$;
—OH; and
—SH; or $R_{49}$ is

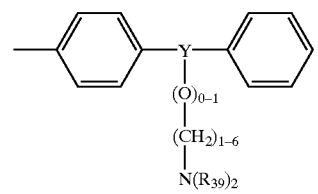

wherein Y is —N— or —CR—;

$R_{29}$ is selected from the group consisting of:
-hydrogen;
—$C_{1-10}$ alkyl;
—$C_{2-10}$ alkenyl;
-aryl;
—$C_{1-10}$ alkyl —O—$C_{1-10}$ alkyl;
—$C_{1-10}$ alkyl —O—$C_{2-10}$ alkenyl; and
—$C_{1-10}$ alkyl or $C_{2-10}$ alkenyl substituted by one or more substituents selected from the group consisting of:
—OH;
-halogen;

—N(R$_{39}$)$_2$;
—CO—N(R$_{39}$)$_2$;
—CO—C$_{1-10}$ alkyl;
—N$_3$;
-aryl;
-heteroaryl;
-heterocyclyl;
—CO-aryl; and
—CO-heteroaryl;
each R$_{39}$ is independently selected from the group consisting of hydrogen and C$_{1-10}$ alkyl; and
each R is independently selected from the group consisting of hydrogen, C$_{1-10}$ alkyl, C$_{1-10}$ alkoxy, halogen and trifluoromethyl,

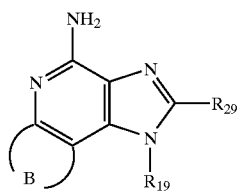

IX(b)

wherein

B is —NR—C(R)$_2$—C(R)$_2$—C(R)$_2$—; —C(R)$_2$—NR—C(R)$_2$—C(R)$_2$—; —C(R)$_2$—C(R)$_2$—NR—C(R)$_2$— or —C(R)$_2$—C(R)$_2$—C(R)$_2$—NR—;

R$_{19}$ is selected from the group consisting of:
-hydrogen;
—C$_{1-20}$ alkyl or C$_{2-20}$ alkenyl that is unsubstituted or substituted by one or more substituents selected from the group consisting of:
-aryl;
-heteroaryl;
-heterocyclyl;
—O—C$_{1-20}$ alkyl;
—O—(C$_{1-20}$ alkyl)$_{0-1}$-aryl;
—O—(C$_{1-20}$ alkyl)$_{0-1}$-heteroaryl;
—O—(C$_{1-20}$ alkyl)$_{0-1}$-heterocyclyl;
—C$_{1-20}$ alkoxycarbonyl;
—S(O)$_{0-2}$—C$_{1-20}$ alkyl;
—S(O)$_{0-2}$—(C$_{1-20}$ alkyl)$_{0-1}$-aryl;
—S(O)$_{0-2}$—(C$_{1-20}$ alkyl)$_{0-1}$-heteroaryl;
—S(O)$_{0-2}$—(C$_{1-20}$ alkyl)$_{0-1}$-heterocyclyl;
—N(R$_{39}$)$_2$;
—N$_3$;
oxo;
—halogen;
—NO$_2$;
—OH; and
—SH; and
—C$_{1-20}$ alkyl—NR$_{39}$—Q—X—R$_{49}$ or —C$_{2-20}$ alkenyl—NR$_{39}$—Q—X—R$_{49}$ wherein Q is —CO— or —SO$_2$—; X is a bond, —O— or —NR$_{39}$— and R$_{49}$ is aryl; heteroaryl; heterocyclyl; or —C$_{1-20}$ alkyl or C$_{2-20}$ alkenyl that is unsubstituted or substituted by one or more substituents selected from the group consisting of:
-aryl;
-heteroaryl;
-heterocyclyl;
—O—C$_{1-20}$ alkyl,
—O—(C$_{1-20}$alkyl)$_{0-1}$-aryl;
—O—(C$_{1-20}$alkyl)$_{0-1}$-heteroaryl;
—O—(C$_{1-20}$alkyl)$_{0-1}$-heterocyclyl;

—C$_{1-20}$ alkoxycarbonyl;
—S(O)$_{0-2}$—C$_{1-20}$ alkyl;
—S(O)$_{0-2}$—(C$_{1-20}$ alkyl)$_{0-1}$-aryl;
—S(O)$_{0-2}$—(C$_{1-20}$ alkyl)$_{0-1}$-heteroaryl;
—S(O)$_{0-2}$—(C$_{1-20}$ alkyl)$_{0-1}$-heterocyclyl;
—N(R$_{39}$)$_2$;
—NR$_{39}$—CO—O—C$_{1-20}$alkyl;
—N$_3$;
oxo;
-halogen;
—NO$_2$;
—OH; and
—SH; or R$_{49}$ is

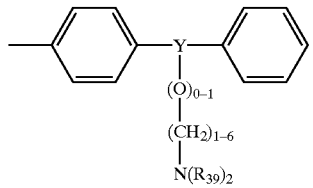

wherein Y is —N— or —CR—;
R$_{29}$ is selected from the group consisting of:
-hydrogen;
—C$_{1-10}$ alkyl;
—C$_{2-10}$ alkenyl;
—aryl
—C$_{1-10}$ alkyl —O—C$_{1-10}$-alkyl;
—C$_{1-10}$ alkyl —O—C$_{2-10}$ alkenyl; and
—C$_{1-10}$ alkyl or C$_{2-10}$ alkenyl substituted by one or more substituents selected from the group consisting of:
—OH;
-halogen;
—N(R$_{39}$)$_2$;
—CO—N(R$_{36}$)$_2$;
—CO—C$_{1-10}$ alkyl;
—N$_3$;
-aryl;
-heteroaryl;
-heterocyclyl;
—CO-aryl; and
—CO-heteroaryl;
each R$_{39}$ is independently selected from the group consisting of hydrogen and C$_{1-10}$ alkyl; and
each R is independently selected from the group consisting of hydrogen, C$_{1-10}$ alkyl, C$_{1-10}$ alkoxy, halogen and trifluoromethyl.

The substituents R$_{11}$–R$_{19}$ above are generally designated "1-substituents", as they are located at the 1-position of the various ring systems. Preferred 1-substituents include alkyl containing one to six carbon atoms and hydroxyalkyl containing one to six carbon atoms. More preferably the 1-substituent is 2-methylpropyl or 2-hydroxy-2-methylpropyl.

The substituents R$_{21}$–R$_{29}$ above are generally designated "2-substituents", due to their placement at the 2-position of the various ring systems. Preferred 2-substituents include hydrogen, alkyl of one to six carbon atoms, alkoxyalkyl wherein the alkoxy moiety contains one to four carbon atoms and the alkyl moiety contains one to four carbon atoms, and hydroxyalkyl of one to four carbon atoms. More preferably the 2-substituent is hydrogen, methyl, butyl, hydroxymethyl, ethoxymethyl or methoxyethyl.

In instances where n can be zero, one, or two, n is preferably zero or one.

As used herein, the terms "alkyl", "alkenyl", and the prefix "-alk" are inclusive of both straight chain and branched chain groups and of cyclic groups, i.e. cycloalkyl and cycloalkenyl. These cyclic groups can be monocyclic or polycyclic and preferably have from 3 to 10 ring carbon atoms. Exemplary cyclic groups include cyclopropyl, cyclopentyl, cyclohexyl and adamantyl. Alkyl and alkenyl groups contain from 1 to 10 (or 2 to 10) carbon atoms unless otherwise specified.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g. O, S, N). Suitable heteroaryl groups include furyl, thienyl, pyridyl, quinolinyl, tetrazolyl, imidazolyl, and so on.

"Heterocyclyl" includes non-aromatic rings or ring systems that contain at least one ring hetero atom (e.g. O, S, N). Exemplary heterocyclic groups include pyrrolidinyl, tetrahydrofuranyl, morpholinyl, thiazolidinyl, imidazolidinyl and the like.

The aryl, heteroaryl and heterocyclyl groups may be unsubstituted or substituted by one or more substituents selected from the group consisting of $C_{1-20}$ alkyl, hydroxy, halogen, $N(R_{10})_2$ where each $R_{10}$ is independently selected from the group consisting of hydrogen, $C_{1-10}$ alkyl, $NO_2$, $C_{1-20}$ alkoxy, $C_{1-20}$ alkylthio, trihalomethyl, $C_{1-20}$ acyl, arylcarbonyl, heteroarylcarbonyl, $(C_{1-10}$ alkyl$)_{0-1}$-aryl, $(C_{1-10}$ alkyl$)_{0-1}$-heteroaryl, nitrile, $C_{1-10}$ alkoxycarbonyl, oxo, arylalkyl wherein the alkyl group has from 1 to 10 carbon atoms, and heteroarylalkyl wherein the alkyl group has from 1 to 10 carbon atoms.

The invention is inclusive of the compounds described herein in any of their pharmaceutically acceptable forms, including salts, isomers such as diastereomers and enantiomers, solvates, polymorphs, and the like.

Of the foregoing IRM compounds, those having the imidazoquinoline structure are preferred. In particular, imidazoquinoline-4-amine compounds of formulas I and V are preferred. The compounds 4-amino-2-ethoxymethyl-α, α-dimethyl-1H-imidazo[4,5-c]quinolin-1-ethanol and 1-(2-methylpropyl)-1H-imidazo[4,5-c]quinolin-4-amine are especially preferred.

The IRM compounds useful in the methods of the invention can be prepared using methods that are known in the art, as seen for example in U.S. Pat. Nos. 4,689,338, 5,389,640, 5,268,376, 4,929,624, 5,266,575, 5,352,784, 5,494,916, 5,482,936, 5,346,905, 5,395,937, 5,756,747, 4,988,815, 5,175,296, 5,741,908, 5,367,076, 5,693,811 and 5,525,612, and in copending U.S. patent application Ser. No. 09/210,114 all of which are incorporated by reference herein.

Maturation of Dendritic Cells

The IRM compounds described above have been found to induce the maturation of DC ex vivo. In general, mature DC display properties such as cytokine secretion, the expression of particular cell surface markers, and an enhanced ability to stimulate T-cells.

Dendritic cells that can be matured using the method of the invention can be obtained from any source, which sources can be readily determined by those of skill in the art. For example, the immature DC can be obtained by isolating the DC from tissues such as blood, spleen, bone marrow, skin (e.g., Langerhans cells) and the like or by inducing the differentiation of monocytes or stem cells using methods known in the art. A preferred method of obtaining DC comprises the cytokine-induced differentiation of human peripheral blood mononuclear cells. This method has been described, for example by Romani et al., *J. Immunol. Methods* 196:137 (1996) and Bender et al., *J. Immunol. Methods* 196:121 (1996). A particularly preferred method comprises culturing CD14+ peripheral blood monocytes with GM-CSF and IL-4 using the method described by Romani, supra.

The DC thus obtained will be in an immature state, generally possessing a high capability for antigen capture and processing, but relatively low T-cell stimulatory capacity. To acquire optimal T-cell stimulating capacity, the DC must be in a stable, mature state. Mature DC can be identified by a number of properties, including their expression of the cell surface marker CD83 and by the behavior displayed during the mixed lymphocyte reaction. In this reaction mature DC will cause increased proliferation of naïve allogeneic T-cells and/or increased production of dendritic cell cytokines. Preferably, the mature DC will induce at least a two-fold increase in the proliferation of naïve allogeneic T-cells and/or will display at least a three-fold increase in the production of dendritic cell cytokines, particularly IL-12 and TNF-α, as compared to DC that have been obtained from the same source but have not been contacted with any exogenous stimuli ("immature DC"). While immature DC may display some of the properties described above, they display them to a much lesser extent than DC which have been matured by exposure to exogenous stimuli such as an imidazoquinoline type IRM compound. The mature DC should be stable and not revert to their immature state, as the immature DC are much less potent stimulators of T-cell activity.

The method of the invention comprises the maturation of DC by stimulating the DC with an imidazoquinoline type IRM in an amount and for a time sufficient to cause the DC to mature. It is understood that the DC are incubated in a tissue culture medium under conditions readily determinable to those of skill in the art. The specific amount of IRM used and the time of exposure will vary according to a number of factors that will be appreciated by those of skill in the art, including the origin of the DC to be matured, the potency and other characteristics of the IRM compound used, and so on. However, it is currently preferred that the IRM be used at a concentration of about 0.1 to about 10 µg/ml, preferably about 0.5 to about 2.0 µg/ml. The IRM compound is solubilized before being added to the DC containing medium, preferably in water or a physiological buffer. However, if necessary the compound can be solubilized in a small amount of an organic solvent such as DMSO and then diluted or added directly to the DC containing medium.

The DC are stimulated by the IRM compound for a sufficient amount of time to allow the DC to become fully mature. This can be determined by periodically withdrawing samples of the DC containing medium and assaying for one of the above described properties, such as secretion of dendritic cell cytokines. In general, the DC can be said to be fully mature when the measured property has attained its maximal level and is no longer increasing with time. Although the time of exposure will vary according to factors understood by those of skill in the art (including but not limited to the origin of the DC, the concentration and potency of the IRM, and so on), in general approximately 16 to 24 hours of stimulation are required for the DC to become fully mature.

Dendritic cells that have been matured by exposure to one or more imidazoquinoline type IRMs express CD83 and display enhanced expression of CD80, CD86 and CD40. In addition, IRM matured DC secrete a number of cytokines, particularly pro-inflammatory cytokines such as TNF-α, IFN-α, IL-6, IL-1, IL-12 p40.

Use of IRM Matured Dendritic Cells

Dendritic cells that have been matured by exposure to imidazoquinoline type IRMs have enhanced antigen presenting ability as compared to immature DC and can be used in a variety of ways to enhance the immune response of a subject. For example, the mature DC can be injected directly into a patient. In this case, the DC are preferably monocyte derived DC wherein the monocytes have been obtained from the same patient.

The DC can also be used in a number of immunotherapies. Examples of such therapies include ex vivo cell transplantation therapies for treating disorders of the immune system, such as AIDS; the ex vivo expansion of T-cells, particularly antigen specific T-cells which can then be used to treat disorders characterized by deterioration of the immune system; the generation of monoclonal antibodies that recognize DC-specific markers; the preparation of antigen activated DC according to methods known in the art; and development of vaccines and vaccine adjuvants.

Preferred uses of DC that have been matured by exposure to one or more imidazoquinoline type IRMs include those that make use of antigen activated DC and/or DC modified antigens. The antigen activated DC, or cellular adjuvants, of the invention are generally prepared by exposing DC matured according to the method of the invention to an antigen. The antigen may be protein, carbohydrate or nucleic acid in nature and may be derived from any suitable source, including neoplastic cells (e.g., tumor cells) and infectious agents (e.g., bacterium, virus, yeast, parasite). Alternatively, the antigen can be derived by recombinant means.

The cellular adjuvant of the invention can be used in the treatment of diseases. For example, cellular adjuvants prepared by exposing the mature DC to tumor derived antigens can be administered to a patient, thereby provoking an anti-tumor immune response in the patient. Similarly, infectious diseases can be treated by administering to the patient cellular adjuvants prepared by exposing the DC to antigens derived from the infectious agent.

Dendritic cells that have been matured by the method of the invention produce cytokines such as IL-12 and IFN-α that favor the generation of Th1 immune responses. The ability to bias the immune response towards the Th 1, as opposed to the Th2, response, can provide a means for treatment of Th2 mediated diseases. Examples of such diseases include asthma; allergic rhinitis; systemic lupus erythematosis; eczema; atopic dermatitis Ommen's syndrome (hyperseosinophilia syndrome); certain parasitic infections such as cutaneous and systemic leishmaniais, toxoplasma infection and trypanosome infection; certain fungal infections, for example candidiasis and histoplasmosis; and certain intracellular bacterial infections such as leprosy and tuberculosis.

Experimental

Materials and Methods

Culture Medium. Complete RPMI (cRPMI) medium was used throughout this study. cRPMI consists of RPMI 1640 with 25 mM HEPES (Life Technologies, Gaithersburg, Md.) supplemented with 10% heat inactivated FCS (Hyclone, Logan, Utah), 1 mM sodium pyruvate, 0.1 mM non-essential amino acids, 1 mM L-glutamine and 50 μg/ml gentamicin sulphate (Life Technologies).

Reagents. Peripheral blood derived CD14+ cells were differentiated into DC using recombinant human GM-CSF and recombinant human IL-4 at 800 U/ml and 25 ng/ml, respectively (R&D Corporation, Minneapolis, Minn.), as described by Romani and Bender, supra. Tetanus toxoid (Calbiochem, La Jolla, Calif.) was solubilized in cRPMI and used at 10 μg/ml. The compound R-848 (S-28463), 4-amino-2-ethoxymethyl-α,α-dimethyl-1H-imidazo[4,5-c]quinoline-1-ethanol, M.W.=314.4, was prepared by 3M Pharmaceuticals, St. Paul, Minn. For cell culture studies, the HCl salt was dissolved in pyrogen-free, sterile water and stored as a stock solution at 4° C. for up to 4 months. Endotoxin levels were below the detectable level [1 pg/mg] in the Limulus amebocyte assay. A stock solution of bacterial LPS from *Escherichia coli* O55:B5 (Sigma Chemical, St. Louis, Mo.) was dissolved at 1 mg/ml in pyrogen-free water and stored at 4° C. until use.

Generation of Monocyte-Derived Dendritic Cells (MO-DC). PBMC were isolated with Histopaque HybriMax-1077 density gradient (Sigma) from healthy volunteers after obtaining informed consent. CD14+ cells were purified by positive selection using CD14+ microbeads in conjunction with the MiniMACS system (Miltenyi Biotech, Auborn, Calif.) by following the manufacturer's instructions. Purity, as assessed by flow cytometry, was greater than 90%. The CD14+ cells were cultured at $2-5 \times 10^6$ cells per 3 ml cRPMI in 6-well plates (Costar, Cambridge, Mass.) with 800 U/ml GM-CSF and 25 ng/ml IL-4 as previously described by Romani and Bender, supra. Fresh medium containing GM-CSF and IL-4 was added every three days. MO-DC were routinely used between days 7 and 8 of culture. As a control, depleted lymphocytes were cultured in the same fashion.

In Vitro MO-DC Stimulation. MO-DC were stimulated with 0.1 to 8 μg/ml R-848 (1 μg/ml=3.2 μM) or 1 μg/ml LPS for 1–96 hours. Cells were subsequently analyzed by flow cytometry for the expression of various cell surface markers, and the cell culture supernatants were analyzed for various cytokines and chemokines by ELISA.

Cell Surface and Intracellular Flow Cytometry. Evaluation of cell surface marker expression was performed by flow cytometric analysis using the following monoclonal antibodies: FITC-conjugated CD1a, clone NA1/34 HLK (Accurate Chemical, Westbury, N.Y.); PE-conjugated CD14, clone MφP9, PE-conjugated CD80, clone L307.4, PE- and FITC-conjugated HLA-DR, clone L243, PE- and FITC-conjugated γ1/γ2a isotype control, clones X40 and X39 (all from Becton Dickinson, Mountain View, Calif.); PE-conjugated CD40, clone EA-5 (Biosource International, Camarillo, Calif.); PE-conjugated CD83, clone HB15a, PE- and FITC-conjugated γ1/γ1 isotype control, clone 679.1Mc7 (Immunotech, Marseille, France), PE-conjugated CD86, clone 2331(Pharmingen, San Diego, Calif.). Cells ($5-10^5$) were incubated for 15 minutes incubation at 4° C. with purified IgD (Becton Dickinson) to block non-specific binding, and then the cells were stained for 30 minutes with the antibodies at 4° C. in PBS containing 10% FCS and 0.1% sodium azide. After washing in PBS, the cells were analyzed using a FACScan flow cytometer and Cell Quest software (Becton Dickinson).

Allogeneic Lymphocyte Activation. T-cells were isolated using T-Cell Purification Columns according to manufacturer's specifications (R&D Systems, Minneapolis, Minn). Allogeneic MO-DC stimulator cells were pulsed for various times with medium alone, R-848, or LPS for 1, 6 or 24 hrs and then washed and treated with 50 μg/ml mitomycin C (Sigma) for 20 minutes at 37° C. Dendritic cells were subsequently washed, resuspended in cRPMI and added at various concentrations ($1-32 \times 10^3$ per well) to purified responder T-cells (1×10$^5$ per well) in 96-well flat-bottomed microtiter plates (BD Labware) in a total volume of 200 μl. Triplicate cultures were maintained at 37° C. for 96 hours after which time cell proliferation was assessed by incorporation of [$^3$H]-thymidine ([$^3$H]-TdR) (Amersham, Arlington Heights, Ill.). Each well received 1 μCi [$^3$H]TdR and was harvested 18 hours later. Results are presented as mean CPM±SEM of triplicate wells. Supernatants were collected from the same cultures prior to pulsing with [$^3$H]TdR and analyzed for IFN-γ, L-5 and IL-2.

Autologous T Cell Activation. Autologous T cells and R-848-treated MO-DC were prepared as described for allogeneic T cell stimulation. MO-DC were cultured with R-848 [2 μg/ml] and tetanus toxoid [10 μg/ml] for 24 hours. The MO-DC were washed and cultured at graded doses with PBMC-derived CD3$^+$ T cells for 7 days. Cell proliferation and analysis were determined as described. Supernatants were also collected; from the same cultures prior to pulsing with [$^3$H]TdR and analyzed for IFN-γ and IL-5.

Cytokine Analysis. Cytokine levels were measured by ELISA. Human TNF-α, IL-12 (p40/p70), IFNγ, IL-4 and IL-2 kits were purchased from Genzyme (Cambridge, Mass.). Human IL-6 kits were obtained from Biosource International (Camarillo, Calif.). Human IL-5, IL-8, MIP-1α, MCP-1 and RANTES were purchased from R&D Systems. All ELISA were run according to manufacturer's specifications. IFN levels were; measured by bioassay (40). IFN-α and IFN-β specific antibodies were used to determine which type I IFN was present in the MO-DC supernatants. Results for all ELISAs are presented in pg/ml, whereas IFN results are presented in U/ml.

Statistical Analysis. Data were analyzed using a paired Student's t-test, and the results were considered statistically significant if p≦0.05.

Figure 1C:
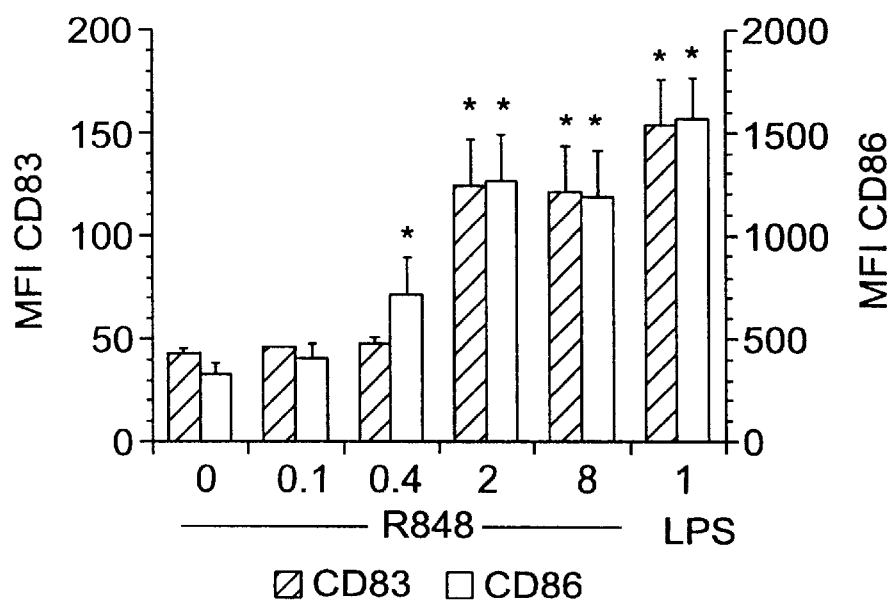
Figure 1B:
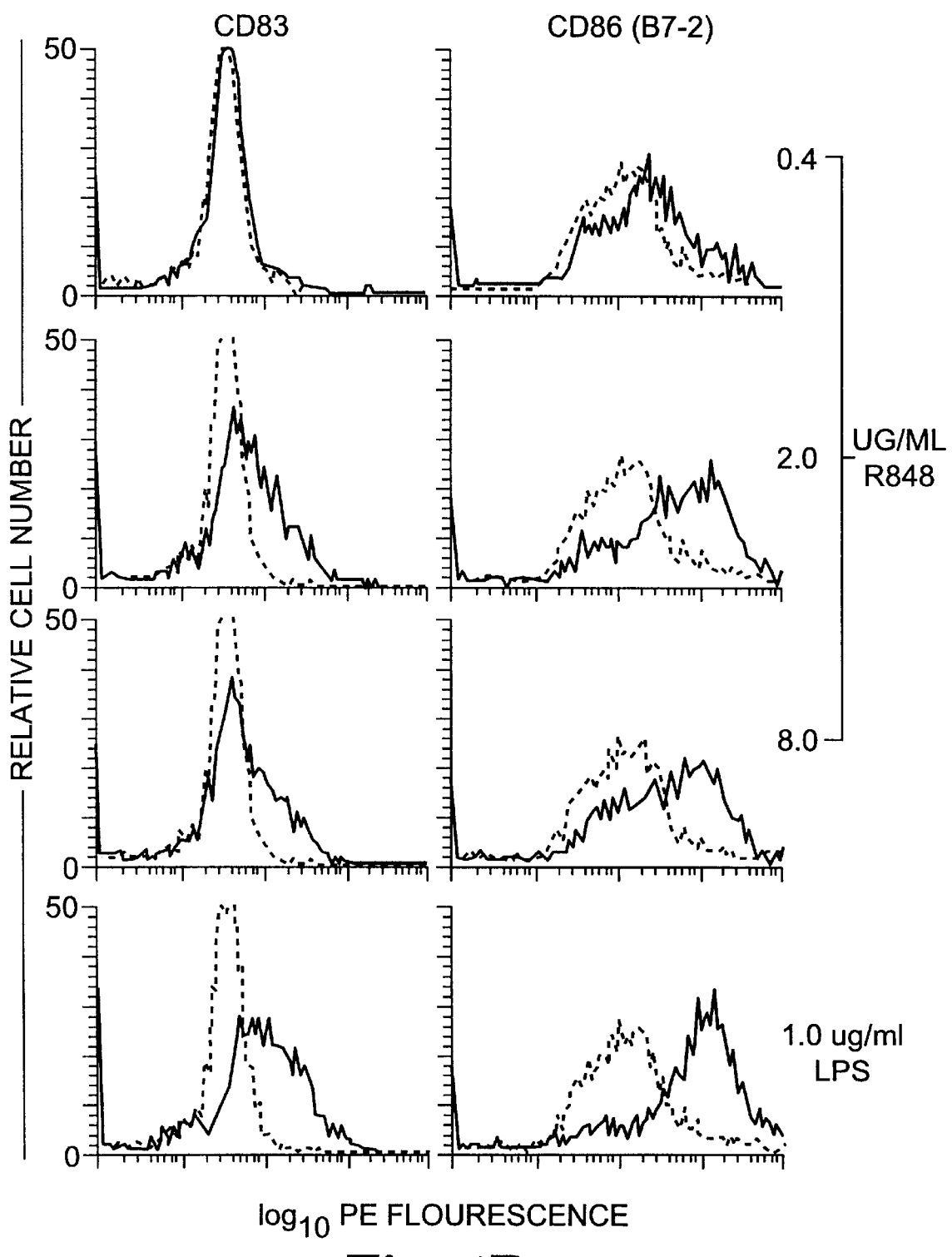

To assess the maturation potential of R-848 on DC, MO-DC were treated with R-848 [0.1–8 μg/ml] or LPS [1 μg/ml] for 24 hours, and cell surface CD83 and CD86 expression were analyzed by flow cytometry on the DC (gated) population as defined by the forward scatter/side scatter characteristics (FIG. 1A). The results in FIG. 1B demonstrate that R-848 enhances the expression of CD83 and CD86 on MO-DC as compared to unstimulated (vehicle) cells. There was no increase in either CD83 or CD86 cell surface expression with 0.1 μg/ml R848. Enhanced CD86 expression is evident with 0.4, 2 and 8 μg/ml R-848. Enhanced cell surface expression of CD83 is seen at 2 and 8 μg/ml R-848. Both CD83 and CD86 cell surface expression are also enhanced with LPS, which has been shown to enhance the expression of these molecules on DC. FIG. 1C represents the quantitative CD83 and CD86 cell surface expression in mean fluorescence intensity (MFI) of R-848 treated MO-DC. R-848 induces an increase of both CD83 and CD86 expression in a dose dependent manner, with CD86 expression increasing between 0.1–0.4 μg/ml R-848. CD83 expression is significantly increased between 0.4–2 μg/ml R-848. Maximal increases in both CD83 and CD86 expression are generated with 2 μg/ml R-848, which corresponds to an average increase of approximately 3- to 4-fold for both CD80 and CD86. Comparatively, maximal CD83 and CD86 cell surface expression induced with R-848 was equivalent to that induced by LPS. Both the relative cell number and MFI data correlate indicating an increased number of cells expressing these antigens in response to R-848.

Figure 2A:
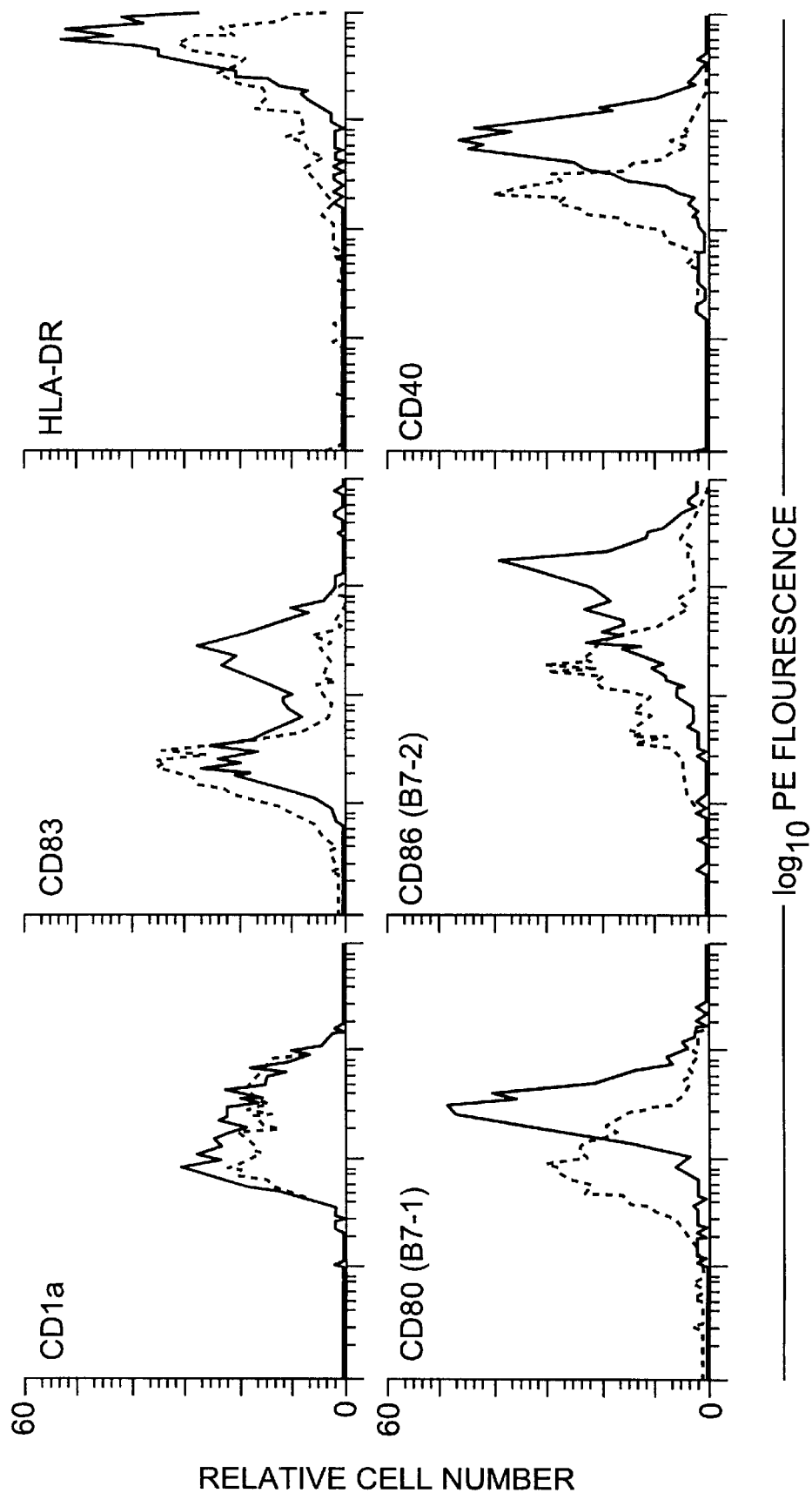
FIG. 2 shows the ability of R-848 to enhance the cell surface expression of co-stimulatory molecules on MO-DC.

In addition to CD83 and CD86, other cell surface molecules indicative of DC maturation were also examined by flow cytometry. MO-DC were cultured with 2 μg/ml R-848 for 24 hours, which gave maximal CD83 and CD86 expression as shown in FIG. 1. The cells were stained for cell surface expression of CD1a, CD80, CD83, CD86, CD40 and HLA-DR. FIG. 2A demonstrates that R-848 also enhances the expression of CD80 and CD40, in addition to CD83 and CD86, as compared to vehicle controls. FIGS. 2B and 2C represent the quantitative differences in cell surface molecule expression. Consistent with the increase in CD83 and CD86 expression, R-848 treatment also induces a 2-fold increase in CD80 and CD40 expression over the vehicle treated MO-DC. Although R-848-induces an increase in cell surface HLA-DR expression (FIGS. 2A and 2C), the increase is not quantitatively significant. Similarly, the R-848-induced decrease in CD1a expression is not statistically significant. These trends in HLA-DR and CD1a expression following R-848 stimulation were seen in all experiments, and in some experiments, the differences were statistical significant between R-848 and vehicle treated cells. LPS used at 1 μg/ml enhanced cell surface expression of CD40, CD80, CD86 and CD83 to similar levels induced by R-848 (data not shown). The results in FIGS. 1 and 2 demonstrate that R-848 induces MO-DC maturation as defined by increased CD83, CD80, CD86 and CD40 expression. These DC maturation markers were also examined after 48, 72 and 96 hour stimulation with R-848, and maximal DC maturation marker expression was obtained after 24 hours in culture with 2 μg/ml R-848.

R-848 Induces the Secretion of Pro-inflammatory Cytokines and Chemokines from Monocyte-Derived Dendritic Cells DC maturation results in the production of various cytokines and chemokines. In addition, numerous cytokines produced by mature DC such as TNF-α and IL-12 can induce or enhance DC maturation. Therefore, we tested if R-848 induces MO-DC cytokine and chemokine secretion characteristic of DC maturation. MO-DC were cultured with various concentrations of R-848 for 24 hours as in FIGS. 1 and 2. The supernatants were analyzed for secreted cytokines and chemokines by ELISA or by bioassay. The results in Table I indicate that MO-DC treated with R-848 produce significantly more TNF-α, IL-6, IL-12, IL-8, MIP-1α and IFN-α as compared to the vehicle control. Although statistically significant levels of all the tested cytokines are obtained with 2 μg/ml R-848, IL-6, IL-8 and IL-12 appear to be induced with R-848 between 0.1–0.4 μg/ml, but the levels are not statistically different than those produced by the vehicle-treated MO-DC. MCP-1 levels were increased with 0.1–8 μg/ml R-848, but not significantly different from the levels produced by the control cells. Neutralizing IFN-α inhibited greater than 95% of the bioactivity, indicating that the IFN induced by R-848 was IFN-α. Similar to R-848, LPS significantly enhanced TNF-α, IL-6, IL-12, MIP-1α and IFN-α as compared to the vehicle control group. The maximal cytokine and chemokine levels induced by LPS are comparable to the maximal levels induced by R-848.

The length of time MO-DC need to be in contact with R-848 for maturation to occur was determined by pulsing the cells with R-848 for various periods of time. Culture supernatants were analyzed for cytokine secretion after various treatment times with R-848 or LPS. TNF-α and IL-12 secretion were used as markers of DC maturation on the basis of the results in Table I and on previous studies. First, MO-DC were cultured with 2 μg/ml R-848 or 1 μg/ml LPS for 1, 6 or 24 hours, and the supernatants were then analyzed for cytokine secretion immediately post culture (Table II, Groups I, II and V). The results in Table II demonstrate that MO-DC produce minimal amounts of TNF-α and IL-12 after one hour stimulation with R-848. A significant increase in TNF-α and IL-12 protein is detected in the supernatants following 6 hour stimulation with R-848. R-848 treatment for 24 hours also induces a significant increase in TNF-α and IL-12 secretion. The LPS groups produced both TNF-α and IL-12 with the same kinetics as the R-848-treated groups, except LPS induced approximately 2-fold more TNF-α than was induced by R-848. LPS treated MO-DC produced approximately 5-fold more IL-12 than R-848 treated MO-DC.

The results in Table II indicate that MO-DC require greater than one hour stimulation with either R-848 or LPS in order to secrete significant levels of TNF-α. and IL-12. Maximal TNF-α secretion is achieved between one and six hours stimulation, and maximal IL-12 secretion requires between six and twenty four hours stimulation with either R-848 or LPS.

Figure 3A:
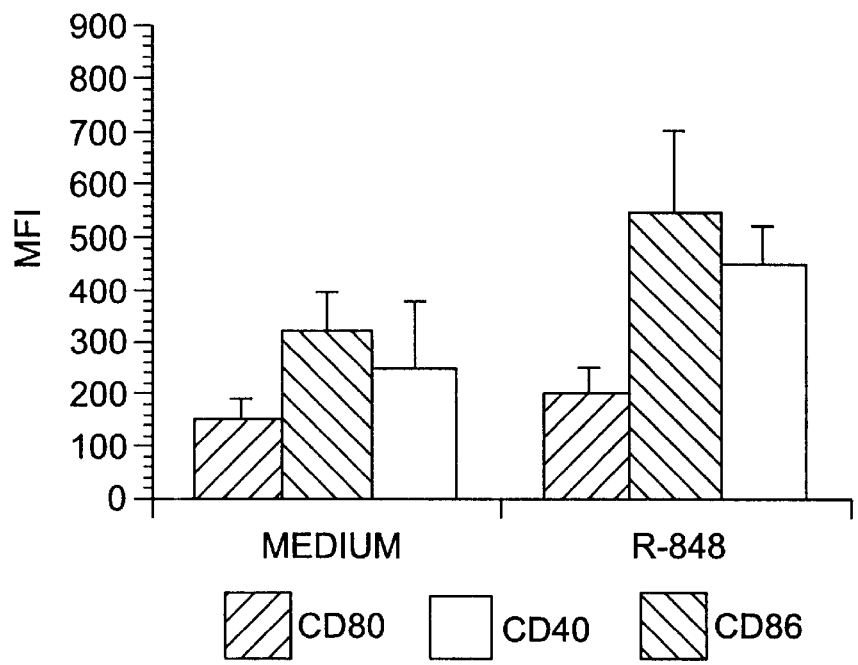
FIG. 3 shows the maturation of DC as measured by cell surface expression of various markers after 6 hours of stimulation with 2 $\mu$g/ml R-848.
Figure 3B:
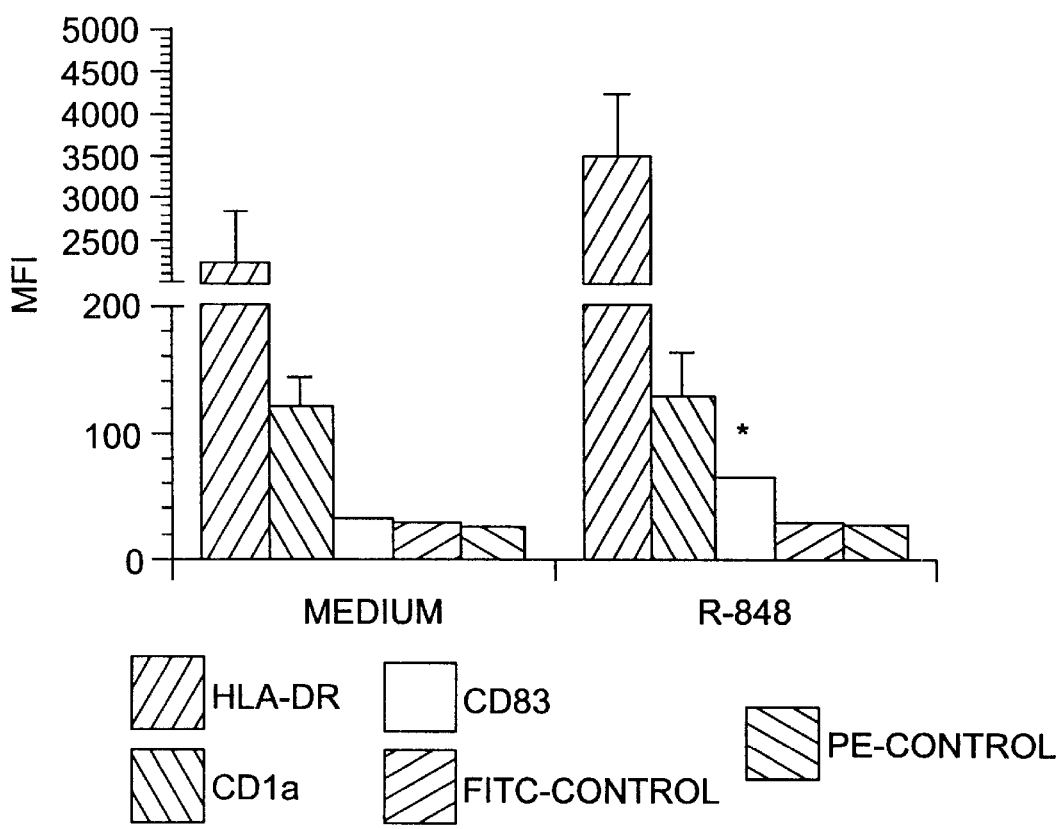

In addition to TNF-α and IL-12 production, cell surface markers of DC maturation were also examined by flow cytometry following R-848 treatment for various times in order to determine the length of time MO-DC need to be in culture with R-848 for optimal maturation marker expression. MO-DC pulsed for one hour with 2 µg/ml R-848 or 1 µg/ml LPS, and then stained for DC maturation markers, did not show enhanced expression of CD83, CD80, CD86, CD40 or HLA-DR. MO-DC pulsed for 6 hours with R-848 and stained immediately for maturation markers show a significant increase in CD83 but not CD80, CD86, CD40 or HLA-DR (FIG. 3A and 3B). Although CD40, CD86 and HLA-DR expression are elevated in the R-848 treated group following 6 hours in culture, the differences are not statistically significant as compared to the medium control. Similar to R-848 treated MO-DC, LPS treated MO-DC showed enhanced CD83 expression, but no change in CD40, CD80, CD86 and HLA-DR expression.

Figure 3C:
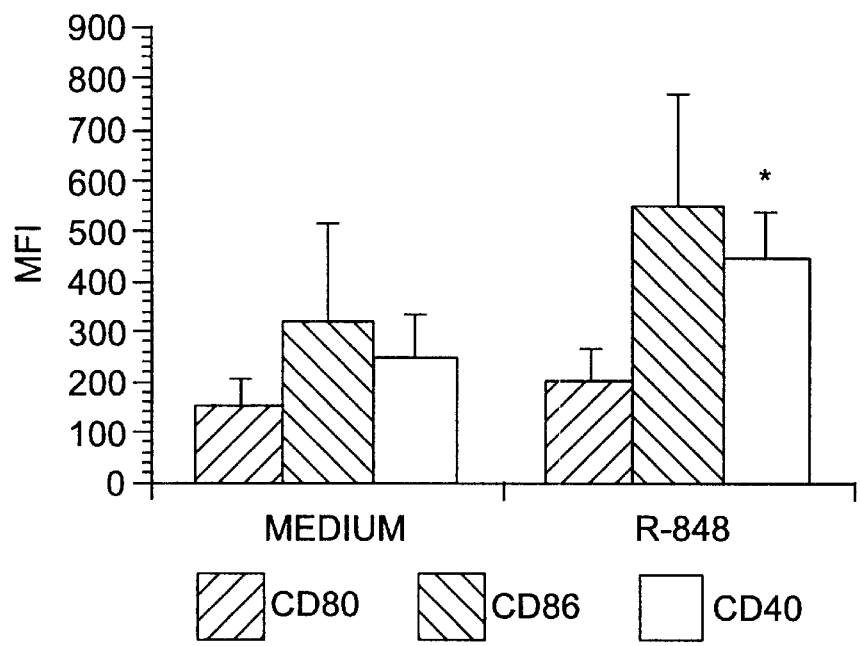
Figure 3D:
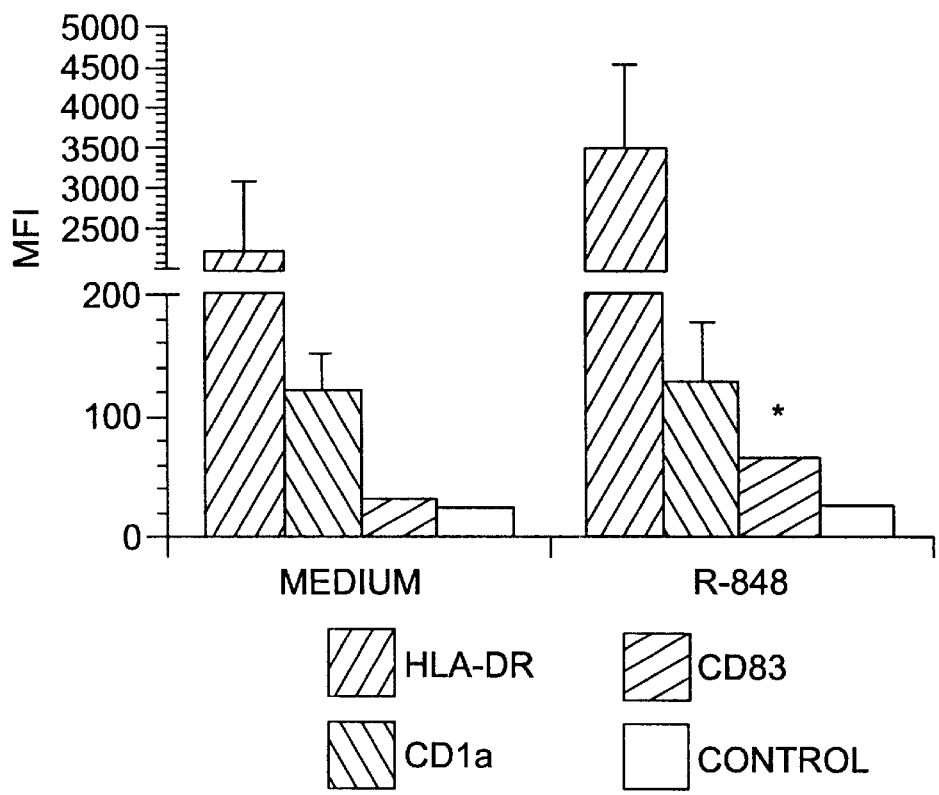

MO-DC were pulsed for 1 or 6 hours with 2 µg/ml R-848 or 1 µg/ml LPS, washed free of stimulus, and then re-cultured for an additional 23 hours (1 hour pulse) or 18 hours (6 hour pulse) before cell surface DC maturation marker determination. MO-DC pulsed for one hour with 2 µg/ml R-848 or 1 µg/ml LPS did not show enhanced expression of CD83, CD80, CD86, CD40 or HLA-DR after 24 hours in culture. MO-DC pulsed for 6 hours with R-848 show a significant increase in CD83 and CD40 expression, but not CD80, CD86 or HLA-DR after 24 hours in culture (FIG. 3C and 3D). The expression of CD86 and HLA-DR markers are elevated above, but not statistically different, than the medium control group. Comparable results were obtained with similarly cultured LPS-stimulated MO-DC.

Figure 4A:
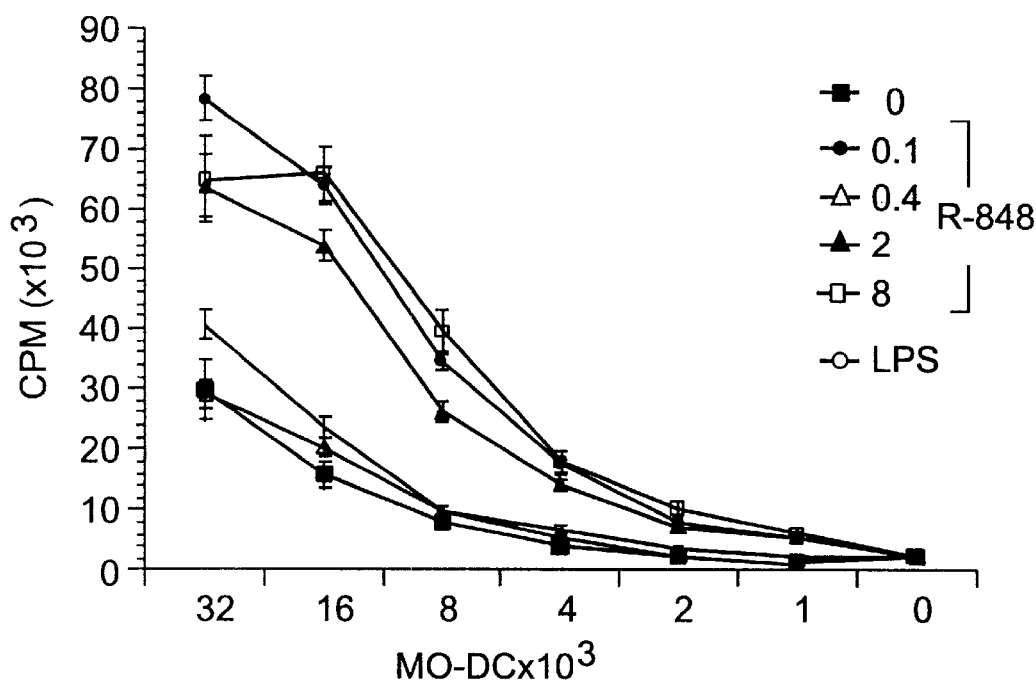
FIG. 4 depicts the results of treating MO-DC with R-848 on T-cell proliferation and T-cell cytokine production as seen by a primary MLR.

Allogeneic T cell Proliferation and T cell Cytokine Secretion are Increased by R-848-treated Monocyte-Derived Dendritic Cells To determine if the functional features of DC were altered by imidazoquinoline-treatment, R-848-stimulated MO-DC were tested in a primary MLR. MO-DC were treated with 0.1–8 µg/ml R-848 or 1 µg/ml LPS. After 24 hours, the MO-DC were washed free of stimulating agent and cultured with allogeneic CD3-enriched peripheral blood T cells for 96 hours, whereby cell proliferation was assessed by [³H] thymidine incorporation. The results in FIG. 4A demonstrate that R-848-treated MO-DC were more efficacious stimulators of allogeneic T cell proliferation than vehicle-treated cells, and R-848-treated cells were as effective as LPS-stimulated cells. A significant difference in T cell proliferation is seen when MO-DC are treated with 2 or 8 µg/ml R-848 as compared to vehicle-treated MO-DC.

Figure 4B:
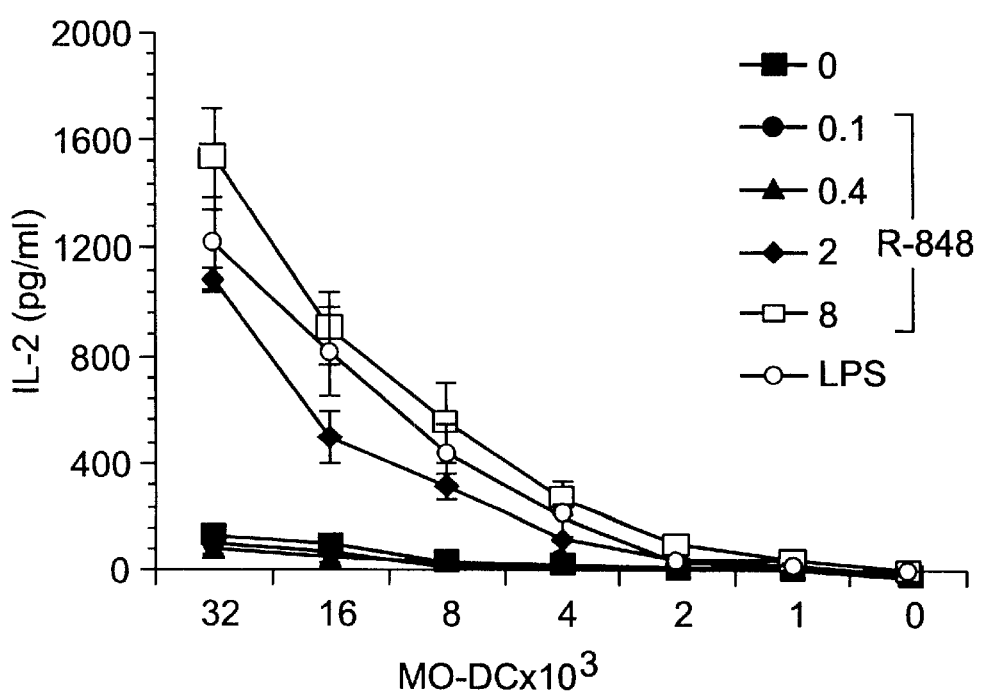
Figure 4C:
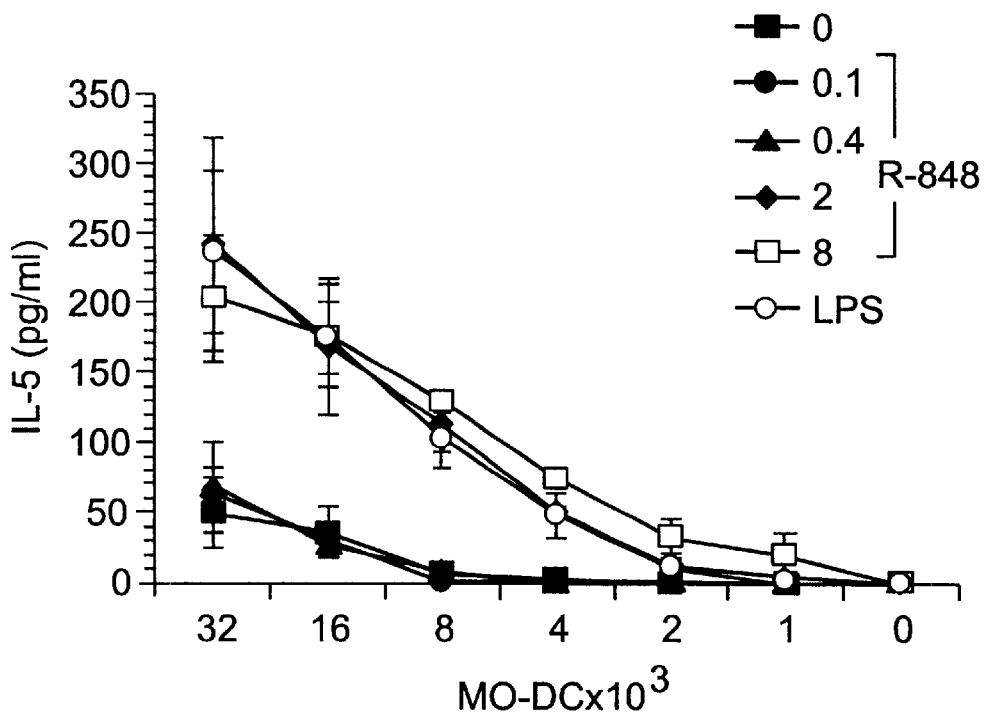
Figure 4D:
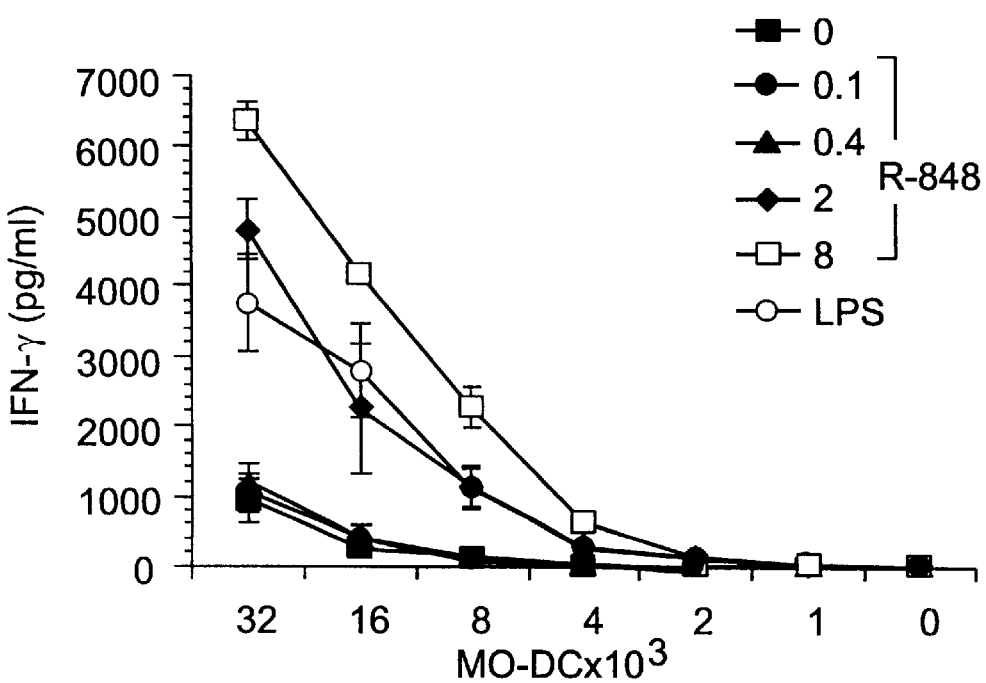

MLR supernatants were analyzed for T cell cytokines following 96 hours of culture. R-848-treated MO-DC enhance IL-2, IL-5 and IFN-γ secretion from allogeneic T cells as compared to the vehicle control group (FIG. 4B–4D). Concordant with the MLR proliferation results in FIG. 4A, a significant 2- to 3-fold enhancement of IL-2, IL-5 and IFN-γ production was induced by cultures containing MO-DC treated with 2 and 8 µg/ml R-848 as compared to the untreated MO-DC cultures. T cell cytokines induced by R-848-stimulated MO-DC were equivalent to cytokine levels induced by LPS-stimulated MO-DC. IL-2, IL-5 and IFN-γ production require MO-DC cultured with T cells, because cultures containing only MO-DC or only T cells did not produce detectable levels of IL-2, IL-5 or IFN-γ. Additionally, T cells cultured in the presence of R-848, without added MO-DC, do not produce IL-2, IL-5 or IFN-γ. These data indicate that R-848 enhances DC function equivalent to that induced by LPS. Although maximal proliferation was induced by MO-DC that were pulsed for 24 hours with R-848, MO-DC treated for 6 hours with R-848 also significantly enhanced allogeneic T cell proliferation as compared to untreated MO-DC. When MO-DC were treated for less than 6 hours with R-848, allogeneic T cell proliferation was not significantly increased as compared to the untreated MO-DC controls.

Figure 5A:
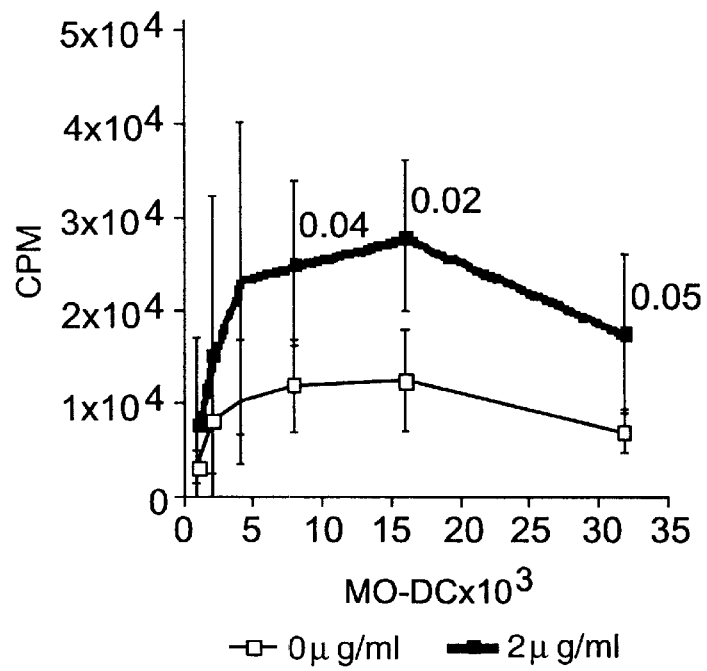
FIG. 5 shows the response of R-848 treated MO-DC to tetanus toxoid.
Figure 5B:
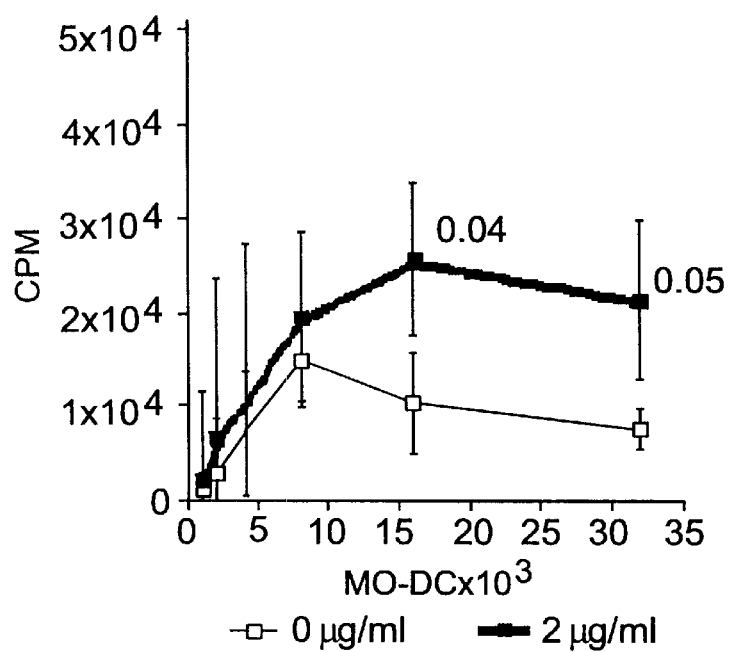
Figure 5C:
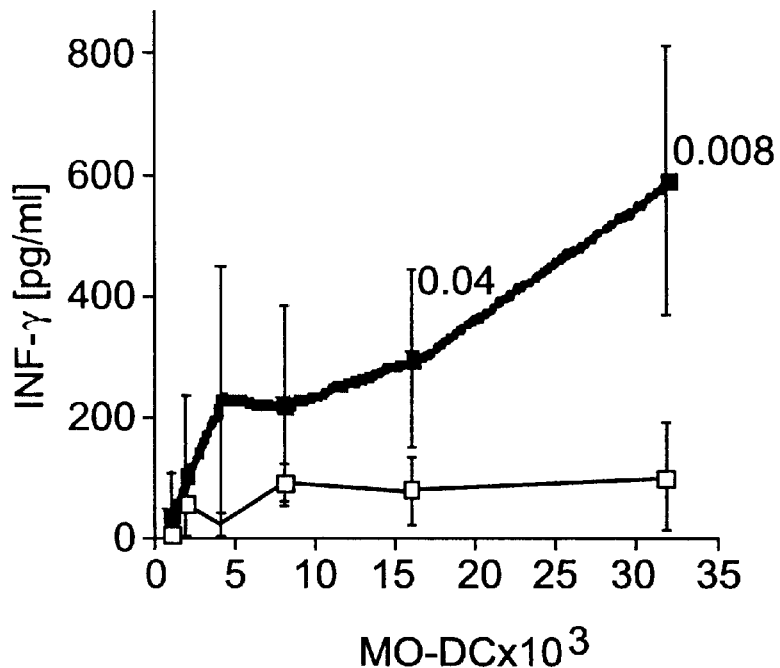
Figure 5D:
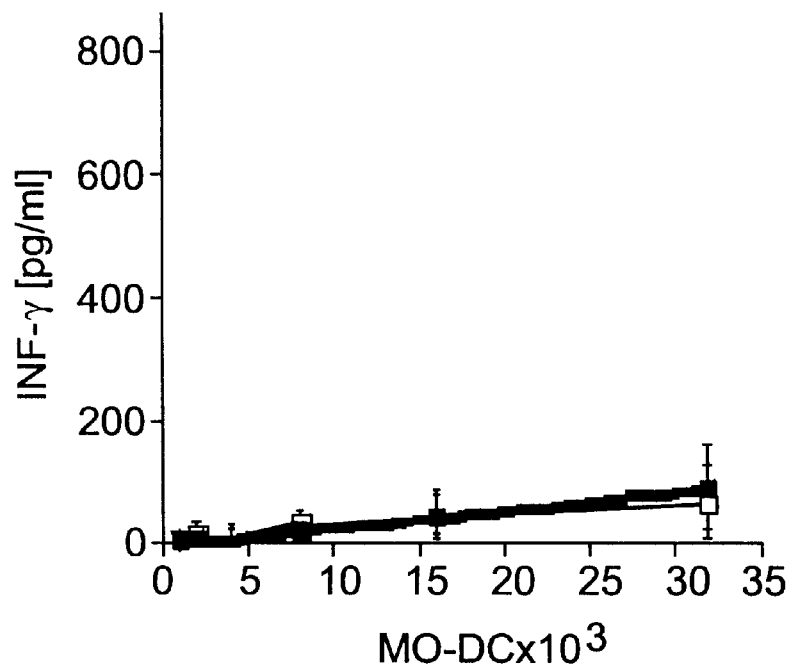

Autologous T cell Proliferation and T cell Cytokine Secretion are Increased by R-848-treated Monocyte-Derived Dendritic Cells The effect of R-848 on MO-DC function was also tested in an autologous (syngeneic) anamnestic response to tetanus toxoid. MO-DC were treated with 2 µg/ml R-848 and 10 µg/ml tetanus toxoid for 24 hours. The MO-DC were washed free of compound and antigen and then cultured with syngeneic CD3-enriched peripheral blood T cells for 7 days at which time proliferation was assessed by [³H]thymidine incorporation. The results in FIG. 5A and 5B indicate that tetanus toxoid-treated MO-DC and untreated MO-DC induced the same amount of syngeneic T cell proliferation. However, R-848-treated MO-DC increased T cell proliferation by 2to 3-fold as compared to the MO-DC that were not treated with R-848. Cytokine secretion was also analyzed from the autologous MO-DC/T cell system. IFN-γ secretion was only detected in the supernatants that contained MO-DC treated with both R-848 and tetanus toxoid (FIGS. 5C and 5D). MO-DC treated with both R-848 and tetanus toxoid produced 4- to 11-fold more IFN-γ than MO-DC cultured only with the tetanus toxoid antigen. IL-5 was not detected in any of the same culture supernatants containing IFN-γ. The data in FIG. 5 indicate that memory T cell IFN-γ secretion, but not proliferation, is enhanced by R-848-treated MO-DC.

DETAILED DESCRIPTION OF THE DRAWINGS

FIG. 1. The immune response modifier R-848 enhances cell surface expression of CD83 and CD86 on monocyte-derived dendritic cells (MO-DC). MO-DC were generated in vitro from CD14⁺ PBMC as described in Materials and Methods. MO-DC ($2\times10^5$) were stimulated with 0.1–8 µg/ml R-848 [0.32–26 µM] or 1 µg/ml LPS for 24 hours. A, The cells were subsequently stained for CD83 and CD86 cell surface expression, and the MO-DC gated population was analyzed by flow cytometry. B, The results are expressed as the relative cell number that stain positively within the gated population. The solid lines indicate R-848 or LPS treatment, and the dotted lines indicate medium (vehicle) control. The results in A and B are representative of six independent experiments from six different donors. C, The results are expressed as the mean fluorescence intensity (MFI)±SEM of six independent experiments from six different donors. *$p \leq 0.05$ FIG. 2. R-848 enhances cell surface expression of co-stimulatory molecules on MO-DC. MO-DC ($2\times10^5$) were stimulated with 2 μg/ml R-848 for 24 hours. The cells were subsequently stained for cell surface expression of CD80, CD86, CD40, HLA-DR, CD83 and CD1a. A, The results are expressed as the relative cell number that stain positively within the MO-DC gated population and are representative of three independent experiments from three different donors. The solid lines indicate R-848 treatment, and the dotted lines indicate medium (vehicle) control. B, C, cultured at graded doses with $1\times10^5$ CD3 enriched syngeneic T cells in triplicate for seven days. A, B, Proliferation was assessed by [$^3$H]thymidine incorporation after seven days. C, D, IFN-γ protein was assessed from the culture supernatants as described in Materials and Methods. The results are expressed as mean pg/ml±SEM of three independent experiments from three different donors. The values indicated above some of the data points represent p-values≦0.05.

TABLE I

R-848 stimulates MO-DC cytokine and chemokine secretion[a]

| Treatment [μg/ml] | IFN-α | TNF-α | IL-6 | IL-8 | IL-12 | MCP-1 | MIP-1α |
|---|---|---|---|---|---|---|---|
| 0 (vehicle) | 3 ± 2 | 5 ± 2 | 3 ± 2 | 305 ± 77 | 27 ± 11 | 1742 ± 646 | 46 ± 46 |
| 0.1 R-848 | 8 ± 3 | 6 ± 3 | 20 ± 12 | 425 ± 132 | 70 ± 21 | 3603 ± 2158 | 57 ± 57 |
| 0.4 R-848 | 8 ± 3 | 14 ± 4 | 399 ± 208 | 5125 ± 2430 | 106 ± 27 | 4864 ± 2213 | 511 ± 314 |
| 2.0 R-848 | 27 ± 7* | 1540 ± 371* | 6729 ± 1888* | 50092 ± 10385* | 15984 ± 3860* | 12941 ± 5802 | 15412 ± 5244* |
| 8.0 R-848 | 41 ± 12* | 2208 ± 240* | 9690 ± 1269* | 66988 ± 11863* | 19640 ± 3966* | 16249 ± 7661 | 25956 ± 5782* |
| 1.0 LPS | 59 ± 12* | 2246 ± 438* | 10134 ± 1687* | 64668 ± 12407* | 15593 ± 2755* | 11006 ± 4485 | 36243 ± 8676* |

[a]MO-DC ($2 \times 10^5$) were cultured for 24 hours in cRPMI containing graded doses of R-848 or LPS at 37° C. with 5% $CO_2$. Culture supernatants were collected and stored at −70° C. until analysis by ELISA or by bioassay. Data are given as mean ± SEM of five independent experiments from five different donors. All values are in pg/ml, except IFN-α which is in U/ml.
*, p ≦ 0.05, as compared to cytokine levels in vehicle control.

The results are expressed as the MFI±SEM of at least three independent experiments from three different donors. *p≦0.05

FIG. 3. Maturation of monocyte-derived dendritic cells requires between 1 and 6 hours stimulation with R-848. MO-DC ($2\times10^5$) were stimulated with 2 μg/ml R-848 for 6 hours. A, B, The cells were subsequently stained for cell surface expression of CD80, CD86, CD40, HLA-DR, CD83 and CD1a. C, D, The cells were extensively washed, re-cultured for an additional 18 hours, and then subsequently stained for cell surface expression of CD80, CD86, CD40, HLA-DR, CD83 and CD1a. The results are expressed as MFI±SEM of three independent experiments from three different donors. *p≦0.05

FIG. 4. T cell proliferation and T cell cytokine production are increased by R-848-treated MO-DC in a primary MLR. MO-DC ($2\times10^5$) were stimulated with 0.1–8 μg/ml R-848 or 1 μg/ml LPS for 24 hours. The cells were extensively washed and cultured at graded doses with $1\times10^5$ CD3 enriched allogeneic T cells in triplicate. A, Proliferation was assessed by [$^3$H]thymidine incorporation after 96 hours. The results are expressed as mean CPM±SEM of three independent experiments from three different donors. Statistically significant differences (p≦0.05) were determined between R-848 [2 and 8 μg/ml] and LPS treated groups as compared to vehicle [0 μg/ml] treated group at $4–32\times10^3$ MO-DC. B-D, IL-2, IL-5 and IFN-γ protein were assessed from the culture supernatants as described in Materials and Methods. The results are expressed as mean pg/ml±SEM of three independent experiments from three different donors. Statistically significant differences (p≦0.05) were determined between R-848 [2 and 8 μg/ml] and LPS treated groups as compared to vehicle [0 μg/ml] treated group at $8–32\times10^3$ MO-DC.

FIG. 5. Autologous T cell proliferation and T cell cytokine secretion are increased by R-848-treated MO-DC in an anamnestic response to tetanus toxoid. MO-DC ($2\times10^5$) were stimulated with 2 μg/ml R-848 and 10 μg/ml tetanus toxoid for 24 hours. The cells were extensively washed and

TABLE II

TNF-α and IL-12 production from MO-DC requires between 1 and 6 hours stimulation with R-848[a]

| Treatment time (hr)[b] | Treatment[c] | TNF-α | IL-12 |
|---|---|---|---|
| 1 | vehicle | 1 ± 1 | 73 ± 37 |
|   | R-848 | 32 ± 10* | 65 ± 18 |
|   | LPS | 51 ± 8* | 44 ± 19 |
| 6 | vehicle | 3 ± 3 | 92 ± 99 |
|   | R-848 | 1053 ± 707* | 4446 ± 2438* |
|   | LPS | 2679 ± 557* | 6160 ± 1109* |
| 24 | vehicle | 3 ± 4 | 107 ± 32 |
|   | R-848 | 335 ± 201* | 13153 ± 5484* |
|   | LPS | 1675 ± 665* | 21167 ± 1050* |

[a]MO-DC ($2 \times 10^5$) were cultured for 24 hours in cRPMI containing graded doses of R-848 or LPS at 37° C. with 5% $CO_2$. Culture supernatants were collected and stored at −70° C. until analysis by ELISA. Data are given as mean pg/ml ± SEM of three independent experiments from three different donors.
[b]Treatment time (hr) is the length of time MO-DC were in culture with R-848 or LPS.
[c]MO-DC were treated for the indicated times with 2 μg/ml R-848, 1 μg/ml LPS or vehicle (PBS).
*, p ≦ 0.05, as compared to the cytokine levels in the vehicle control.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the methods, compositions and structures described herein, but rather by the language of the claims that follow.

What is claimed is:

1. A method of in vitro maturation of immature dendritic cells comprising stimulating said immature dendritic cells with an immune response modifying compound wherein said compound contains an imidazoquinoline; imidazopyridine; 6,7 fused cycloalkylimidazopyridine; 1,2 bridged imidazoquinoline; imidazonaphthyridine; or imidazotetrahydronaphthyridine ring system.

2. The method of claim 1 wherein the immature dendritic cells are monocyte-derived dendritic cells.

3. The method of claim 1 wherein the immature dendritic cells are obtained by incubating human peripheral blood mononuclear cells with GM-CSF and IL-4.

4. The method of claim 1 wherein the immune response modifying compound containing an imidazoquinoline ring system comprises a 1H-imidazo [4,5-c]quinoline-4-amine.

5. The method of claim 1 wherein the immune response modifying compound containing an imidazoquinoline ring system is a compound of the formula:

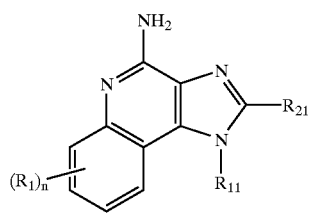

I wherein
- $R_{11}$ is selected from the group consisting of alkyl of one to ten carbon atoms, hydroxyalkyl of one to six carbon atoms, acyloxyalkyl wherein the acyloxy moiety is alkanoyloxy of two to four carbon atoms or benzoyloxy, and the alkyl moiety contains one to six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that if said benzene ring is substituted by two of said moieties, then said moieties together contain no more than six carbon atoms;
- $R_{21}$ is selected from the group consisting of hydrogen, alkyl of one to eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that when the benzene ring is substituted by two of said moieties, then the moieties together contain no more than six carbon atoms; and
- each $R_1$ is independently selected from the group consisting of alkoxy of one to four carbon atoms, halogen, and alkyl of one to four carbon atoms, and n is an integer from 0 to 2, with the proviso that if n is 2, then said $R_1$ groups together contain no more than six carbon atoms; or a pharmaceutically acceptable salt or solvate thereof.

6. The method of claim 1 wherein the immune response modifying compound containing an imidazoquinoline ring system is 4-amino-2-ethoxymethyl-γ,γ-dimethyl-1H-imidazo[4,5-c]quinolin-1-ethanol.

7. The method of claim 1 wherein the resulting mature dendritic cells induce at least a two-fold increase in the proliferation of naïve allogeneic T-cells and/or display at least a three-fold increase in the production of one or more cytokines selected from the group consisting of TNF-α, IFN-α, IL-6, IL-1, IL-12, IL-8, MCP-1, and MCP-1α.

8. The method of claim 1 wherein the immature dendritic cells are stimulated for about 16 to about 24 hours.

9. A method of enhancing the antigen presenting ability of dendritic cells comprising stimulating said dendritic cells with an the immune response modifying compound wherein said compound contains an imidazoquinoline; imidazopyridine; 6,7 fused cycloalkylimidazopyridine; 1,2 bridged imidazoquinoline; imidazonaphthyridine; or imidazotetrahydronaphthyridine ring system.

10. The method of claim 1 wherein the immune response modifying compound containing an imidazoquinoline ring system is a compound of the formula:

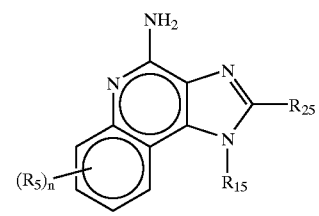

V wherein
- $R_{15}$ is selected from the group consisting of: hydrogen; straight chain or branched chain alkyl containing one to ten carbon atoms and substituted straight chain or branched chain alkyl containing one to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; straight chain or branched chain alkenyl containing two to ten carbon atoms and substituted straight chain or branched chain alkenyl containing two to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;
- $R_{25}$ is

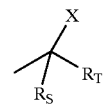

wherein
- $R_S$ and $R_T$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen;

X is selected from the group consisting of alkoxy containing one to four carbon atoms, alkoxyalkyl wherein the alkoxy moiety contains one to four carbon atoms and the alkyl moiety contains one to four carbon atoms, hydroxyalkyl of one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, alkylthio of one to four carbon atoms; and $R_5$ is selected from the group consisting of hydrogen, straight chain or branched chain alkoxy containing one to four carbon atoms, halogen, and straight chain or branched chain alkyl containing one to four carbon atoms, and n is an integer from 0 to 2, with the proviso that if n is 2, then said $R_5$ groups together contain no more than six carbon atoms, or a pharmaceutically acceptable salt or solvate thereof.

* * * * *

UNITED STATES PATENT AND TRADEMARK OFFICE
CERTIFICATE OF CORRECTION

PATENT NO. : 6,558,951 B1 Page 1 of 1
DATED : May 6, 2003
INVENTOR(S) : Tomai, Mark A.

It is certified that error appears in the above-identified patent and that said Letters Patent is hereby corrected as shown below:

Column 13,
Line 29, delete "$C_{1-10}$" and insert in place thereof -- $C_{1-20}$ --.

Column 23,
Line 56, delete "γ, γ" and insert in place thereof -- α, α --.

Signed and Sealed this

Twenty-third Day of December, 2003

JAMES E. ROGAN
*Director of the United States Patent and Trademark Office*